US011234995B2

(12) United States Patent
Nakamori et al.

(10) Patent No.: US 11,234,995 B2
(45) Date of Patent: Feb. 1, 2022

(54) α-SYNUCLEIN EXPRESSION INHIBITOR

(71) Applicants: OSAKA UNIVERSITY, Osaka (JP); NATIONAL UNIVERSITY CORPORATION TOKYO MEDICAL AND DENTAL UNIVERSITY, Tokyo (JP); NATIONAL INSTITUTES OF BIOMEDICAL INNOVATION, HEALTH AND NUTRITION, Osaka (JP)

(72) Inventors: Masayuki Nakamori, Osaka (JP); Hideki Mochizuki, Osaka (JP); Satoshi Obika, Osaka (JP); Takanori Yokota, Tokyo (JP); Tetuya Nagata, Tokyo (JP); Yuya Kasahara, Osaka (JP)

(73) Assignees: OSAKA UNIVERSITY, Osaka (JP); NATIONAL UNIVERSITY CORPORATION TOKYO MEDICAL AND DENTAL UNIVERSITY, Tokyo (JP); NATIONAL INSTITUTES OF BIOMEDICAL INNOVATION, HEALTH AND NUTRITION, Osaka (JP)

( * ) Notice: Subject to any disclaimer, the term of this patent is extended or adjusted under 35 U.S.C. 154(b) by 27 days.

(21) Appl. No.: 16/068,163

(22) PCT Filed: Jan. 5, 2017

(86) PCT No.: PCT/JP2017/000185
§ 371 (c)(1),
(2) Date: Jul. 5, 2018

(87) PCT Pub. No.: WO2017/119463
PCT Pub. Date: Jul. 13, 2017

(65) Prior Publication Data
US 2019/0008886 A1 Jan. 10, 2019

(30) Foreign Application Priority Data
Jan. 7, 2016 (JP) ............................ JP2016-002103

(51) Int. Cl.
C12N 15/11 (2006.01)
A61K 31/712 (2006.01)
C07K 14/47 (2006.01)
C12N 15/113 (2010.01)
C07H 21/02 (2006.01)
C12N 15/09 (2006.01)
(Continued)

(52) U.S. Cl.
CPC ............ *A61K 31/712* (2013.01); *A61P 25/16* (2018.01); *A61P 25/28* (2018.01); *C07H 21/02* (2013.01); *C07K 14/47* (2013.01); *C12N 15/09* (2013.01); *C12N 15/113* (2013.01); *C12N 2310/3231* (2013.01); *Y02P 20/55* (2015.11)

(58) Field of Classification Search
CPC .................. C12N 2310/3231; C12N 2310/341
See application file for complete search history.

(56) References Cited

U.S. PATENT DOCUMENTS 6,403,566 B1 6/2002 Wang
8,541,562 B2 * 9/2013 Obika .................... C07H 19/06
536/23.1
9,127,280 B2 9/2015 Obika et al.
(Continued)

FOREIGN PATENT DOCUMENTS

JP 2011155914 8/2011
JP 2011155914 A 8/2011
(Continued)

OTHER PUBLICATIONS

Fluiter et al., On the in vitro and in vivo properties of four locked nucleic acid nucleotides incorporated into an anti-H-ras antisense oligonucleotide, ChemBioChem, vol. 6, pp. 1104-1109. (Year: 2005).*

(Continued)

*Primary Examiner* — Dana H Shin
(74) *Attorney, Agent, or Firm* — Renner, Otto, Boisselle & Sklar, LLP

(57) ABSTRACT

The present invention can provide a nucleic acid medicine which has a higher effect and a more prolonged effect of inhibiting the expression of α-synudein can be provided. Disclosed is the oligonucleotide or a pharmacologically acceptable salt thereof, the oligonucleotide containing at least one nucleoside structure represented by Formula (I): (where each of Base and A are defined substituent or structure), can bind to an α-synudein gene, has activity for inhibiting expression of the α-synudein gene, and is complementary to the α-synudein gene, and the oligonucleotide has a length of twelve to twenty bases.

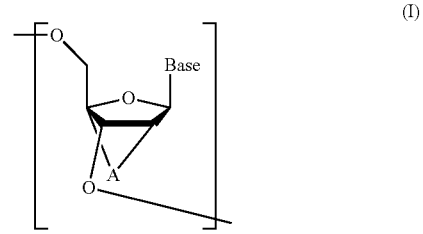

13 Claims, 3 Drawing Sheets
Specification includes a Sequence Listing.

(51) Int. Cl.
*A61P 25/28* (2006.01)
*A61P 25/16* (2006.01)

(56) References Cited

U.S. PATENT DOCUMENTS

| | | | |
|---|---|---|---|
| 9,611,479 | B2 | 4/2017 | Obika et al. |
| 2005/0059617 | A1 | 3/2005 | Imanishi et al. |
| 2005/0186591 | A1 | 8/2005 | Bumcrot et al. |
| 2012/0208991 | A1 | 8/2012 | Obika et al. |
| 2014/0005252 | A1 | 1/2014 | Bennett et al. |
| 2014/0120158 | A1 | 5/2014 | Montefeltro et al. |
| 2014/0323709 | A1 | 10/2014 | Obika et al. |
| 2015/0266917 | A1 | 9/2015 | Obika et al. |

FOREIGN PATENT DOCUMENTS

| | | |
|---|---|---|
| JP | 2015165772 | 9/2015 |
| JP | 2015165772 A | 9/2015 |
| WO | 0206297 | 1/2002 |
| WO | 2015125783 | 8/2015 |
| WO | 2016017422 | 2/2016 |
| WO | 2016017422 A1 | 2/2016 |

OTHER PUBLICATIONS

Straarup et al., Short locked nucleic acid antisense oligonucleotides potently reduce apolipoprotein B mRNA and serum cholesterol in mice and non-human primates, Nucleic Acids Research, vol. 38, pp. 7100-7111. (Year: 2010).*

Kinoh et al. BBRC, 2006, vol. 341, pp. 1088-1095.
Sapru et al. Exp Neurol, 2006, vol. 198, pp. 382-390.
Gorbatyuk et al. Mol Ther, 2010, vol. 18, pp. 1450-1457.
Khodr et al. Brain Res, 2011, vol. 1395, pp. 94-107.
Lewis et al. Mol Neurodegener, 2008, vol. 3, pp. 19.
Cooper et al. Mov Disord, 2014, vol. 29, pp. 1476-1485.
McCormack et al. PLoS One, 2010, vol. 5, pp. e12122.
Tetrahedron Letters, 1981, vol. 22. pp. 1859-1862.
Neurobiology of Aging, 2008, vol. 29, pp. 574-585.
Takashi Osawa et al., "Shinki Rokuinkan Kakyogata Kakusan no Gosei Oyobi Sono Bussei Hyoka", Dai 40 Kai Abstracts Symposium on Progress in Organic Reactions and Synthesis, 2014, p. 122, (Previously submitted) and its partial English translation.
Yoshiyuki Hari et al., "Shinki 6-inkan Kakyogata Thymidine o Fukumu Oligo-kakusan no Gosei Oyobi Kino Hyoka", Dai 44 Kai Book of Abstracts, Congress of Heterocyclic Chemistry, 2014, pp. 21 to 22.
Takashi Osawa et al., "Shinki Rokuinkan Kakyogata Kakusan no Gosei Oyobi Sono Bussei Hyoka", Dai 40 Kai Abstracts Symposium on Progress in Organic Reactions and Synthesis, 2014, p. 122.
PCT/JP2017/000185; PCT International Search Report and Written Opinion of the International Searching Authority dated Mar. 9, 2017.
PCT/JP2017/000185; PCT International Preliminary Examination Report dated Aug. 3, 2017.
Yoshiyuki Hari et al., "Shinki 6-inkan Kakyogata Thymidine o Fukumu Oligo-kakusan no Gosei Oyobi Kino Hyoka", Dai 44 Kai Book of Abstracts, Congress of Heterocyclic Chemistry, 2014, pp. 21 to 22 and its Machine Translation. (reference previously submitted).

* cited by examiner

α-SYNUCLEIN EXPRESSION INHIBITOR

The present application is a U.S. National Stage Application under 35 USC § 371 of International Application No. PCT/JP2017/000185, filed 5 Jan. 2017, published as WO 2017/119463 A1 on 13 Jul. 2017, which in turn claims priority to Japanese Application No. 2016-002103, filed 7 Jan. 2016, the entirety of both of which are incorporated herein by reference.

TECHNICAL FIELD

The present invention relates to an α-synudein expression inhibitor, and more specifically relates to an α-synudein expression inhibitor using an artificial nucleic acid.

BACKGROUND ART

Parkinson's disease (PD) can be classified into sporadic Parkinson's disease and hereditary Parkinson's disease.

Sporadic Parkinson's disease is a progressive neurodegenerative disease. The prevalence rate for sporadic Parkinson's disease is one in a thousand. Dementia occurs with advanced sporadic Parkinson's disease. Such dementia is dementia with Lewy bodies, which can only be treated using a symptomatic treatment. The aggregation and accumulation of α-synudein in the brain considered to be the cause of dementia with Lewy bodies.

Hereditary Parkinson's disease makes up 5 to 10% of Parkinson's disease cases, and it is thought that the PARK 4 gene among pathogenic genes PARK 1 to PARK 20 is involved. Hereditary Parkinson's disease in which the PARK 4 gene is involved exhibits an autosomal dominant pattern of inheritance, and several tens of patients who suffer from hereditary Parkinson's disease are present in Japan. Regarding hereditary Parkinson's disease in which the PARK 4 gene is involved, an excessive number of normal α-synudein genes are present, and thus dementia occurs with the parkinsonian symptoms.

α-Synudein is a protein constituted by 140 amino acid residues, and is an amyloid protein having no specific native structure. α-Synudein is involved in the accumulation and release of synaptic vesicles. An α-synudein knockout (KO) mouse has pathologically no apparent abnormalities, and can exhibit a neuroprotective action against MPTP (1-methyl-4-phenyl-1,2,3,6-tetrahydropyridine), which serves as a neurotoxin.

α-Synudein is a main component of Lewy bodies involved in diseases such as Parkinson's disease and dementia with Lewy bodies (DLB). When α-synudein staining was performed on autopsied brains for the purpose of Braak staging for an analysis of PD autopsied brains, and the development of the disease was contrasted with α-synudein lesions, it was revealed that the aggregation of α-synudein in nerve cells was the main cause of the lesions. When α-synudein fibrils were administered to an α-synudein transgenic (Tg) mouse, the lesions developed using these fibrils as cores, and abnormal α-synudein was also observed outside the cells (prion-like extracellular transmission).

The following describes the clinical condition of Parkinson's disease. The aggregation of abnormal α-synudein in the nerve cells causes the degeneration of the nerve cells in the substantia nigra of the mesencephalon, and the production of dopamine thus decreases, leading to the impairment of the motor functions or cognitive functions. With a conventional symptomatic treatment, neurodegeneration progresses gradually, and in order to address a decrease in the production of dopamine, L-dopa is administered for the supplementation of dopamine or dopamine agonists are administered for the promotion of dopamine secretion.

An attempt has been made to use nucleic acid medicines for α-synudein knockdown targeting the aggregation of abnormal α-synudein in the nerve cells.

Regarding nucleic acid medicines for inhibiting excessive α-synudein, use of adeno associated virus (AAV) ribozyme in rats (Non-Patent Document 1), use of lentivirus-shRNA in rats (Non-Patent Document 2), use of AAV-shRNA in rats (Non-Patent Documents 3 and 4), use of naked siRNA in mice (Non-Patent Document 5), use of exosome siRNA in mice (Non-Patent Document 6), and use of siRNA (2-O-Me) in monkeys (Non-Patent Document 7) have been reported. However, there are problems in that viruses are used in Non-Patent Documents 1 to 4, the effects are lost at an early stage in Non-Patent Documents 5 and 6, and insufficient effects are exhibited in Non-Patent Document 7.

Moreover, use of artificial nucleic acids to inhibit the expression of the α-synuclein gene has been reported (Patent Document 1). In Patent Document 1, nucleosides modified with 2'-O-methoxyethyl (MOE) are used. In addition, in Patent Document 1, oligonucleotides are administered by injection using striatal bolus injection.

RELATED ART DOCUMENTS

Patent Documents

Patent Document 1: JP 2014-501507A

Non-Patent Documents

Non-Patent Document 1: Kinoh et al. BBRC, 2006, vol. 341, pp. 1088-95

Non-Patent Document 2: Sapru et al. Exp Neurol, 2006, vol. 198, pp. 382-90

Non-Patent Document 3: Gorbatyuk et al. Mol Ther, 2010, vol. 18, pp. 1450-7

Non-Patent Document 4: Khodr et al. Brain Res, 2011, vol. 1395, pp. 94-107

Non-Patent Document 5: Lewis et al. Mol Neurodegener, 2008, vol. 3, pp. 19

Non-Patent Document 6: Cooper et al. Mov Disord, 2014, vol. 29, pp. 1476-85

Non-Patent Document 7: McCormack et al. PLoS One, 2010, vol. 5, pp. e12122

SUMMARY OF THE INVENTION

Problem to be Solved by the Invention

The present invention was made to solve the above-described problems, and it is an object thereof to provide a nucleic acid medicine having a higher effect and a more prolonged effect of inhibiting the expression of α-synudein.

Means for Solving the Problem

The present invention provides an oligonucleotide or a pharmacologically acceptable salt thereof, the oligonucleotide containing at least one nucleoside structure represented by Formula (I):

[Chemical Formula 1]

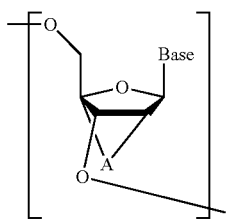

where Base represents a purin-9-yl group that may have any one or more substituents selected from group α, or a 2-oxo-1,2-dihydropyrimidin-1-yl group that may have any one or more substituents selected from group α, the group α consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms, and A is a divalent group represented by:

[Chemical Formula 2]

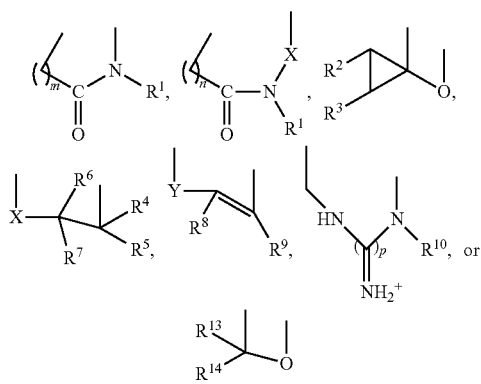

where $R^1$ represents a hydrogen atom, a $C_1$ to $C_7$ alkyl group that may be branched or form a ring, a $C_2$ to $C_7$ alkenyl group that may be branched or form a ring, a $C_3$ to $C_{12}$ aryl group that may have any one or more substituents selected from group α and that may contain a hetero atom, an aralkyl group having a $C_3$ to $C_{12}$ aryl moiety that may have any one or more substituents selected from group α and that may contain a hetero atom, or a protecting group for an amino group on nucleic acid synthesis;

$R^2$ and $R^3$ are independently a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom, or $R^2$ and $R^3$ are taken together to represent —$(CH_2)_q$— (where q is an integer from 2 to 5);

$R^4$ and $R^5$ are independently a group selected from the group consisting of a hydrogen atom; a hydroxy group; a $C_1$ to $C_7$ alkyl group that may be branched or form a ring; a $C_1$ to $C_7$ alkoxy group that may be branched or form a ring; an amino group; and an amino group protected by a protecting group for nucleic acid synthesis, or $R^4$ and $R^5$ are taken together to represent =$C(R^{11})R^{12}$ (where $R^{11}$ and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group);

$R^6$ and $R^7$ are independently a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^8$ represents a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^9$ is a hydrogen atom, a hydroxy group, $C_1$ to $C_7$ alkyl group that may be branched or form a ring, a $C_1$ to $C_7$ alkoxy group that may be branched or form a ring, an amino group, or an amino group protected by a protecting group for nucleic acid synthesis;

$R^{10}$ is a hydrogen atom or a guanidino group;

$R^{13}$ and $R^{14}$ are independently a group selected from the group consisting of a hydrogen atom; a hydroxy group; $C_1$ to $C_7$ alkyl group that may be branched or form a ring; a $C_1$ to $C_7$ alkoxy group that may be branched or form a ring; an amino group; and an amino group protected by a protecting group for nucleic acid synthesis;

m is an integer from 0 to 2;

n is an integer from 0 to 1;

p is 1 when $R^{10}$ is a hydrogen atom or p is 0 when $R^{10}$ is a guanidino group;

X is an oxygen atom, a sulfur atom, or an amino group; and

Y is an oxygen atom or a sulfur atom, wherein the oligonucleotide can bind to an α-synudein gene, has activity for inhibiting expression of the α-synudein gene, and is complementary to the α-synudein gene, and the oligonucleotide has a length of twelve to twenty bases.

In an embodiment, the oligonucleotide can bind to a target region comprising the base sequence from position 99 to position 123 in SEQ ID No.1, and is complementary to at least a portion of the target region, the portion being a region of twelve to twenty bases in length.

In an embodiment, the 3' end of the target region corresponds to position 118, position 121, or position 123 in the base sequence of SEQ ID No.1.

In an embodiment, the oligonucleotide includes (a) a base sequence that is a portion of the base sequence shown in SEQ ID No.3, or (b) a base sequence obtained through deletion, substitution, addition, or insertion of one or two bases in the base sequence of the item (a).

In a further embodiment, the base sequence of the item (b) is a base sequence obtained through deletion, substitution, addition, or insertion of one base in the base sequence of the item (a).

In an embodiment, the 5' end of the oligonucleotide corresponds to the first, third, or sixth base in SEQ ID No.3.

In an embodiment, the oligonucleotide has a length of fifteen to eighteen bases.

In an embodiment, the oligonucleotide is a gapmer including a gap region of six to ten bases, a 5' wing of three to five bases, and a 3' wing of three to five bases, the gap region is located between the 5' wing and the 3' wing, and the 5' wing and the 3' wing each have at least one nucleoside structure represented by Formula (I).

In a further embodiment, the gap region has eight to ten bases, the 5' wing and the 3' wing each have three bases, and the 5' wing and the 3' wing each contain at least two nucleoside structures represented by Formula (I).

The nucleoside structure represented by Formula (I) is a structure represented by:

[Chemical Formula 3]

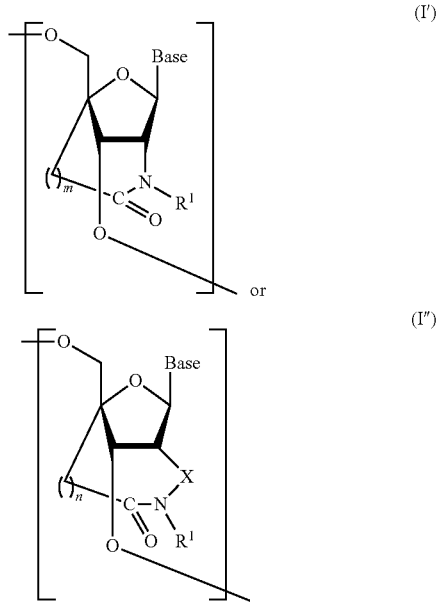

in an embodiment.

In an embodiment, the nucleoside structure represented by Formula (I) is the structure represented by Formula (I') where m is 0, and $R^1$ is a hydrogen atom, a methyl group, an ethyl group, an n-propyl group, an isopropyl group, a phenyl group, or a benzyl group.

The present invention also provides an α-synudein expression inhibitor containing the oligonucleotide or the pharmacologically acceptable salt thereof as an active component.

Furthermore, the present invention provides a pharmaceutical composition containing the oligonucleotide or the pharmacologically acceptable salt thereof as an active component.

In an embodiment, the pharmaceutical composition is used for treatment or prevention of α-synudein excess symptom.

In an embodiment, the pharmaceutical composition is used for treatment or prevention of Parkinson's disease or dementia with Lewy bodies.

In addition, the present invention provides a method for inhibiting expression of α-synudein, the method including a step of administering the oligonucleotide or the pharmacologically acceptable salt thereof to an individual.

Moreover, the present invention provides a method for treating or preventing α-synudein excess symptom, the method including a step of administering the oligonucleotide or the pharmacologically acceptable salt thereof to an individual.

Furthermore, the present invention provides a method for treating or preventing Parkinson's disease or dementia with Lewy bodies, the method including a step of administering the oligonucleotide or the pharmacologically acceptable salt thereof to an individual.

Effects of the Invention

According to the present invention, an oligonucleotide which has a higher effect and a more prolonged effect of inhibiting the expression of α-synudein is provided. According to the present invention, the oligonucleotide can also exhibit the effect of inhibiting α-synudein even when administered through intraspinal administration, which is a commonly used administration route in clinical application.

DETAILED DESCRIPTION

Figure 1:
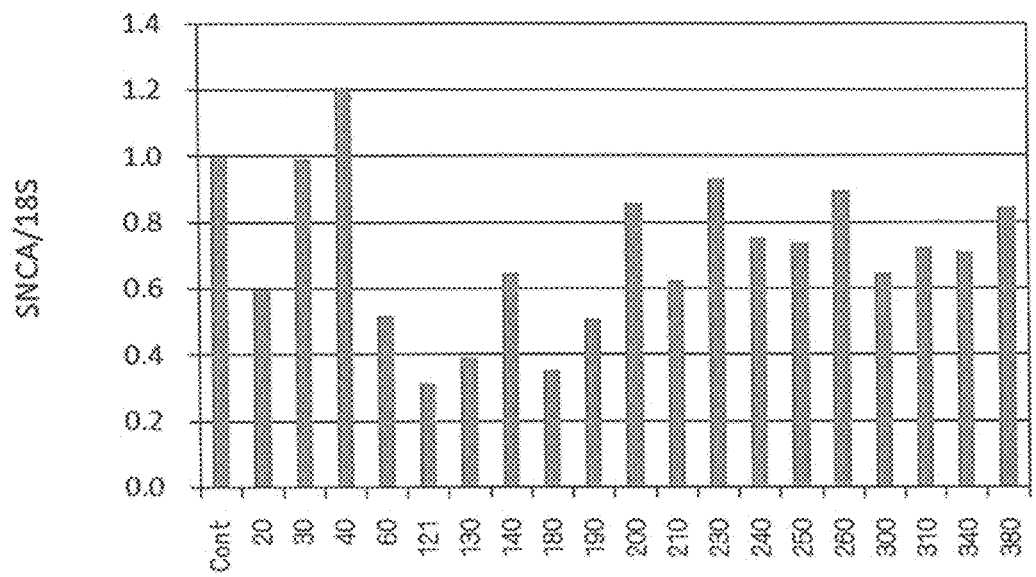
FIG. 1 is a graph showing the amounts of mRNA after the transfection of antisense oligonucleotides (ASOs) into HEK293T cells in Example 3.

The following definitions shall apply throughout the specification.

The term "$C_1$ to $C_6$ linear alkyl group", as used herein, refers to any linear alkyl group having 1 to 6 carbon atoms and specifically a methyl group, an ethyl group, an n-propyl group, an n-butyl group, an n-pentyl group, or an n-hexyl group.

The term "$C_1$ to $C_6$ linear alkoxy group", as used herein, encompasses alkoxy groups having any linear alkyl group having 1 to 6 carbon atoms, and examples of the $C_1$ to $C_6$ linear alkoxy group include a methyloxy group, an ethyloxy group, an n-propyloxy group, and the like. The term "$C_1$ to $C_6$ linear or branched alkoxy group", as used herein, encompasses alkoxy groups having any linear or branched alkyl group having 1 to 6 carbon atoms, and examples of the $C_1$ to $C_6$ linear or branched alkoxy group include a methyloxy group, an ethyloxy group, an n-propyloxy group, an isopropyloxy group, an n-butyloxy group, an isobutyloxy group, a tert-butyloxy group, an n-pentyloxy group, an isopentyloxy group, and the like.

The term "$C_1$ to $C_6$ linear alkylthio group", as used herein, encompasses alkylthio groups having any linear alkyl group having 1 to 6 carbon atoms, and examples of the $C_1$ to $C_6$ linear alkylthio group include a methylthio group, an ethylthio group, an n-propylthio group, and the like. The term "$C_1$ to $C_6$ linear or branched alkylthio group", as used herein, encompasses alkylthio groups having any linear or branched alkyl group having 1 to 6 carbon atoms, and examples of the $C_1$ to $C_6$ linear or branched alkylthio group include a methylthio group, an ethylthio group, an n-propylthio group, an isopropylthio group, an n-butylthio group, an isobutylthio group, a tert-butylthio group, an n-pentylthio group, an isopentylthio group, and the like.

The term "$C_1$ to $C_6$ cyanoalkoxy group", as used herein, refers to a group in which at least one hydrogen atom included in the linear alkoxy group having 1 to 6 carbon atoms mentioned above is substituted with a cyano group.

The term "$C_1$ to $C_6$ linear alkylamino group", as used herein, encompasses a group in which one or two of hydrogen atoms included in an amino group is substituted with any linear alkyl group having 1 to 6 carbon atoms, and examples of the $C_1$ to $C_6$ linear alkylamino group include a methylamino group, a dimethylamino group, an ethylamino group, a methylethylamino group, a diethylamino group, and the like. The term "$C_1$ to $C_6$ linear or branched alkylamino group", as used herein, encompasses a group in which one or two of hydrogen atoms included in an amino group is substituted with any linear or branched alkyl group having 1 to 6 carbon atoms, and examples of the $C_1$ to $C_6$ linear or branched alkylamino group include a methylamino group, a dimethylamino group, an ethylamino group, a methylethylamino group, a diethylamino group, an n-propylamino group, a di-n-propylamino group, an isopropylamino group, a di-isopropylamino group, and the like.

The term "$C_1$ to $C_7$ alkyl group that may be branched or form a ring", as used herein, encompasses any linear alkyl groups having 1 to 7 carbon atoms, any branched alkyl groups having 3 to 7 carbon atoms, and any cyclic alkyl groups having 3 to 7 carbon atoms. It may be simply referred to as "lower alkyl group". Examples of any linear alkyl groups having 1 to 7 carbon atoms include a methyl group, an ethyl group, an n-propyl group, an n-butyl group, an n-pentyl group, an n-hexyl group, and an n-heptyl group, examples of any branched alkyl groups having 3 to 7 carbon atoms include an isopropyl group, an isobutyl group, a tert-butyl group, an isopentyl group, and the like, and examples of any cyclic alkyl groups having 3 to 7 carbon atoms include a cyclobutyl group, a cyclopentyl group, a cyclohexyl group, and the like.

The term "$C_2$ to $C_7$ alkenyl group that maybe branched or form a ring", as used herein, encompasses any linear alkenyl groups having 2 to 7 carbon atoms, any branched alkenyl groups having 3 to 7 carbon atoms, and any cyclic alkenyl groups having 3 to 7 carbon atoms. It may be simply referred to as "lower alkenyl group". Examples of any linear alkenyl groups having 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, a 1-hexenyl group, and the like, examples of any branched alkenyl groups having 3 to 7 carbon atoms include an isopropenyl group, a 1-methyl-1-propenyl group, a 1-methyl-2-propenyl group, a 2-methyl-1-propenyl group, a 2-methyl-2-propenyl group, a 1-methyl-2-butenyl group, and the like, and examples of any cyclic alkenyl groups having 3 to 7 carbon atoms include a cyclobutenyl group, a cyclopentenyl group, a cyclohexenyl group, and the like.

The term "$C_1$ to $C_7$ alkoxy group that may be branched or form a ring", as used herein, encompasses any linear alkoxy groups having 1 to 7 carbon atoms, any branched alkoxy groups having 3 to 7 carbon atoms, and any cyclic alkoxy groups having 3 to 7 carbon atoms. It may be simply referred to as "lower alkoxy group". Examples of any linear alkoxy groups having 1 to 7 carbon atoms include a methoxy group, an ethoxy group, an n-propoxy group, an n-butyloxy group, an n-pentyloxy group, an n-hexyloxy group, and an n-heptyloxy group, examples of any branched alkoxy groups having 3 to 7 carbon atoms include an isopropoxy group, an isobutyloxy group, a tert-butyloxy group, an isopentyloxy group, and the like, and examples of any cyclic alkyl groups having 3 to 7 carbon atoms include a cyclobutyloxy group, a cyclopentyloxy group, a cyclohexyloxy group, and the like.

The term "$C_3$ to $C_{12}$ aryl group that may contain a hetero atom", as used herein, encompasses any aryl groups having 6 to 12 carbon atoms and consisting of only hydrocarbons and any heteroaryl groups having 3 to 12 carbon atoms in which at least one carbon atom constituting the ring structure of the aryl groups was substituted with a hetero atom (e.g., a nitrogen atom, an oxygen atom, and a sulfur atom as well as a combination of these). Examples of the aryl groups having 6 to 12 carbon atoms include a phenyl group, a naphthyl group, an indenyl group, an azulenyl group, and the like, and the heteroaryl groups having 3 to 12 carbon atoms include a pyridyl group, a pyrrolyl group, a quinolyl group, an indolyl group, an imidazolyl group, a furyl group, a thienyl group, and the like.

Examples of the term "aralkyl group having a $C_3$ to $C_{12}$ aryl moiety that may contain a hetero atom", as used herein, include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, a 3-thienylpropyl group, and the like.

Examples of the term "acyl group", as used herein, include aliphatic acyl groups and aromatic acyl groups. Specifically, examples of the aliphatic acyl groups include alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, a 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group and a heneicosanoyl group; carboxylated alkylcarbonyl groups such as a succinoyl group, a glutaroyl group, and an adipoyl group; halogeno lower alkylcarbonyl groups such as a chloroacetyl group, a dichloroacetyl group, a trichloroacetyl group, and a trifluoroacetyl group; lower alkoxy lower alkylcarbonyl groups such as a methoxyacetyl group; and unsaturated alkylcarbonyl groups such as a (E)-2-methyl-2-butenoyl group. Examples of the aromatic acyl groups include arylcarbonyl groups such as a benzoyl group, an α-naphthoyl group, and a ß-naphthoyl group; halogeno-arylcarbonyl groups such as a 2-bromobenzoyl group and a 4-chlorobenzoyl group; lower alkylated arylcarbonyl groups such as a 2,4,6-trimethylbenzoyl group and a 4-toluoyl group; lower alkoxylated arylcarbonyl groups such as a 4-anisoyl group; carboxylated arylcarbonyl groups such as a 2-carboxybenzoyl group, 3-carboxybenzoyl group, and a 4-carboxybenzoyl group; nitrated arylcarbonyl groups such as a 4-nitrobenzoyl group and a 2-nitrobenzoyl group; lower alkoxycarbonylated arylcarbonyl groups such as a 2-(methoxycarbonyl) benzoyl group; and arylated arylcarbonyl groups such as a 4-phenylbenzoyl group. Preferably the acyl group is a formyl group, an acetyl group, a propionyl group, a butyryl group, an isobutyryl group, a pentanoyl group, a pivaloyl group, or a benzoyl group.

Examples of the term "silyl group", as used herein, include tri-lower alkylsilyl groups such as a trimethylsilyl group, a triethylsilyl group, an isopropyldimethylsilyl group, a t-butyldimethylsilyl group, a methyldiisopropylsilyl group, a methyl di-t-butylsilyl group, and a triisopropylsilyl group; and tri-lower alkylsilyl groups substituted with one or two aryl groups such as a diphenylmethylsilyl group, a butyldiphenylbutylsilyl group, a diphenylisopropylsilyl group, and a phenyldiisopropylsilyl group. Preferably the silyl group is a trimethylsilyl group, a triethylsilyl group, a triisopropylsilyl group, a t-butyldimethylsilyl group, or a 1-butyldiphenylsilyl group, more preferably a trimethylsilyl group.

The term "halogen atom", as used herein, includes, for example, a fluorine atom, a chlorine atom, a bromine atom, and an iodine atom. Preferably, the halogen atom is a fluorine atom or a chlorine atom.

The term "protective group" in phrases "a protective group for an amino group on nucleic acid synthesis", "a protective group for a hydroxyl group on nucleic acid synthesis", "a hydroxyl group protected by a protective group for nucleic acid synthesis", "a phosphate group protected by a protective group for nucleic acid synthesis", and "a mercapto group protected by a protective group for nucleic acid synthesis", as used herein, is not limited to specific groups as far as the protective group can stably protect an amino group, a hydroxyl group, a phosphate group, or a mercapto group during nucleic acid synthesis. Specifically, the protective group refers to those which are stable in acid or neutral condition and may be cleaved by chemical methods such as hydrogenolysis, hydrolysis, electrolysis, and photodissociation. Examples of such protective groups include lower alkyl groups, lower alkenyl groups, acyl groups, tetrahydropyranyl or tetrahydrothiopyranyl groups, tetrahydrofuranyl or tetrahydrothiofuranyl groups, silyl groups, lower alkoxymethyl groups, lower alkoxylated lower alkoxymethyl groups, halogeno lower alkoxymethyl groups, lower alkoxylated ethyl groups, halogenated ethyl groups, methyl groups substituted with one to three aryl groups, "methyl groups substituted with one to three aryl groups having the aryl ring substituted with a lower alkyl group, a lower alkoxy group, a halogen atom, or a cyano group", lower alkoxycarbonyl groups, "aryl groups substituted with a halogen atom, a lower alkoxy group, or a nitro group", "lower alkoxycarbonyl groups substituted with a halogen atom or a tri-lower alkylsilyl group", alkenyloxycarbonyl groups, "aralkyloxycarbonyl groups having aryl rings that may be substituted with a lower alkoxy or a nitro group", "lower alkyloxycarbonyl groups substituted with a cyano group", "benzene sulphonyl groups substituted with any of one to four nitro groups", and the like.

More specifically, examples of the tetrahydropyranyl groups or tetrahydrothiopyranyl groups include a tetrahydropyran-2-yl group, a 3-bromotetrahydropyran-2-yl group, a 4-methoxytetrahydropyran-4-yl group, a tetrahydrothiopyran-4-yl group, a 4-methoxytetrahydrothiopyran-4-yl group, and the like. Examples of the tetrahydrofuranyl groups or tetrahydrothiofuranyl groups include a tetrahydrofuran-2-yl group and a tetrahydrothiofuran-2-yl group. Examples of the lower alkoxymethyl groups include a methoxymethyl group, a 1,1-dimethyl-1-methoxymethyl group, an ethoxymethyl group, a propoxymethyl group, an isopropoxymethyl group, a butoxymethyl group, a t-butoxymethyl group, and the like. Examples of the lower alkoxylated lower alkoxymethyl groups include a 2-methoxyethoxymethyl group and the like. Examples of the halogeno lower alkoxymethyl groups include a 2,2,2-trichloroethoxymethyl group, a bis(2-chloroethoxy)methyl group, and the like. Examples of the lower alkoxylated ethyl groups include a 1-ethoxyethyl group, a 1-(isopropoxy) ethyl group, and the like. Examples of the halogenated ethyl groups include a 2,2,2-trichloroethyl group and the like. Examples of the methyl groups substituted with one to three aryl groups include a benzyl group, an α-naphthylmethyl group, a ß-naphthylmethyl group, a diphenylmethyl group, a triphenylmethyl group, an α-naphthyldiphenylmethyl group, a 9-anthrylmethyl group, and the like. Examples of the "methyl groups substituted with one to three aryl groups having aryl rings substituted with a lower alkyl group, a lower alkoxy group, a halogen atom, or a cyano group" include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, a 4-cyanobenzyl group, and the like. Examples of the lower alkoxycarbonyl groups include a methoxycarbonyl group, an ethoxycarbonyl group, a t-butoxycarbonyl group, an isobutoxycarbonyl group, and the like. Examples of the "aryl groups substituted with a halogen atom, a lower alkoxy group, or a nitro group" include a 4-chlorophenyl group, a 2-fluorophenyl group, a 4-methoxyphenyl group, a 4-nitrophenyl group, a 2,4-dinitrophenyl group, and the like. Examples of the "lower alkoxycarbonyl groups substituted with a halogen atom or a tri-lower alkylsilyl group" include a 2,2,2-trichloroethoxycarbonyl group, a 2-trimethylsilyl ethoxycarbonyl group, and the like. Examples of the alkenyloxycarbonyl groups include a vinyloxycarbonyl group, an aryloxycarbonyl group, and the like. Examples of the "aralkyloxycarbonyl groups having an aryl ring that may be substituted with a lower alkoxy or a nitro group" include a benzyloxycarbonyl group, a 4-methoxybenzyloxycarbonyl group, a 3,4-dimethoxybenzyloxycarbonyl group, a 2-nitrobenzyloxycarbonyl group, a 4-nitrobenzyloxycarbonyl group, and the like. Examples of the "lower alkyloxycarbonyl groups substituted with a cyano group" include a cyanoethoxycarbonyl group, and the like. Examples of the "benzene sulphonyl groups substituted with any of one to four nitro groups" include a 2-nitrobenzenesulphonyl group, a 2,4-dinitrobenzenesulphonyl group, and the like.

The "protective group for an hydroxyl group on nucleic acid synthesis" is preferably an aliphatic acyl group, an aromatic acyl group, a methyl group substituted with one to three aryl groups, a "methyl group substituted with one to three aryl groups having aryl rings substituted with a lower alkyl, a lower alkoxy, a halogen, or a cyano group", or a silyl group, and more preferably an acetyl group, a benzoyl group, a benzyl group, a p-methoxybenzoyl group, a dimethoxytrityl group, a monomethoxytrityl group, or a tert-butyldiphenylsilyl group. The protective group in the phrase "a hydroxyl group protected by a protective group for nucleic acid synthesis" is preferably an aliphatic acyl group, an aromatic acyl group, "a methyl group substituted with one to three aryl groups", "an aryl group substituted with a halogen atom, lower alkoxy group, or a nitro group", a lower alkyl group, or a lower alkenyl group, and more preferably a benzoyl group, a benzyl group, a 2-chlorophenyl group, a 4-chlorophenyl group, or a 2-propenyl group. The "protective group for an amino group on nucleic acid synthesis" is preferably an acyl group, and more preferably a benzoyl group. The "protective group" in the phrase "a phosphate group protected by a protective group for nucleic acid synthesis" is preferably a lower alkyl group, a lower alkyl group substituted with a cyano group, an aralkyl group, "an aralkyl group having an aryl ring substituted with a nitro group or a halogen atom", or "an aryl group substituted with a lower alkyl group, a halogen atom, or a nitro group", and more preferably a 2-cyanoethyl group, a 2,2,2-trichloroethyl group, a benzyl group, a 2-chlorophenyl group, or a 4-chlorophenyl group. The number of the protecting group constituting "a phosphate group protected by a protective group for nucleic acid synthesis" may be one or more. The "protective group" in the phrase "a mercapto group protected by a protective group for nucleic acid synthesis" is preferably an aliphatic acyl group or an aromatic acyl group, and more preferably a benzoyl group.

Herein, among the groups represented by —P $(R^{24})R^{25}$ (where $R^{24}$ and $R^{25}$ each independently represent a hydroxyl group, a hydroxyl group protected by a protective group for nucleic acid synthesis, a mercapto group, a mercapto group protected by a protective group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group), the ones where $R^{24}$ can be represented by $OR^{24a}$ and $R^{25}$ can be represented by $NR^{25a}$ are referred to as a "phosphoramidite group". The phosphoramidite groups include, preferably, groups represented by the formula —P(OC$_2$H$_4$CN)(N($_1$Pr)$_2$) or the formula —P(OCH$_3$)(N ($_1$Pr)$_2$). In these formulas, $_1$Pr represents an isopropyl group.

The term "nucleoside" as used herein encompasses a "nucleoside" in which a purine base or a pyrimidine base binds to sugar, as well as those in which a heteroaromatic ring and an aromatic hydrocarbon ring other than purine and pyrimidine, serving as a substitute for a purine base or a pyrimidine base, bind to sugars. A natural nucleoside is also referred to as "native nucleoside". A modified non-natural nucleoside is also referred to as "modified nucleoside", and in particular, a nucleotide in which a sugar moiety is modified is referred to as "sugar-modified nucleoside". The term "nucleotide" means a compound obtained through binding of a phosphate group to sugar of a nucleoside.

The term "oligonucleotide" as used herein refers to a polymer of "nucleotides" in which two to fifty of the same or different "nucleosides" are bound via phosphodiester bonds or other bonds, and encompasses natural oligonucleotides and non-natural oligonucleotides. Preferable examples of the non-natural "oligonucleotides" include sugar derivatives with sugar moieties modified, thioated derivatives with phosphate diester moieties thioated; esters with terminal phosphate moieties esterified; and amides in which amino groups on purine bases are amidated. The sugar derivatives with sugar moieties modified are more preferable.

The term "antisense oligonucleotide" (AON) as used herein refers to an oligonucleotide that is complementary to mRNA, an mRNA precursor, or ncRNA (non-coding RNA) of a target gene and is constituted by single-stranded DNA, single-stranded RNA, and/or analogues thereof. The antisense oligonucleotide forms a double-stranded product together with target mRNA, a target mRNA precursor, or target ncRNA, and thus suppresses the functions of the mRNA, mRNA precursor, or ncRNA. The "antisense oligonucleotide" encompasses antisense oligonucleotides that are completely complementary to target mRNA, a target mRNA precursor, or target ncRNA. Antisense oligonucleotides in which one or several mismatches are present are also encompassed as long as they can bind to mRNA, an mRNA precursor, or ncRNA and suppress the functions thereof. The term "analogues of DNA or RNA" means molecules having a structure similar to that of DNA or RNA An example thereof is a peptide nucleic acid (PNA). The term "ncRNA" (non-coding RNA) collectively refers to RNA that functions without being translated into protein. Examples thereof include ribosomal RNA, transfer RNA, and miRNA.

The term "salt thereof", as used herein, refers to salts of compounds represented by the formula (II) below according to the present invention. Examples of these salts include metal salts including alkaline metal salts such as sodium salts, potassium salts, and lithium salts, alkaline earth metal salts such as calcium salts and magnesium salts, aluminum salts, iron salts, zinc salts, cuprous salts, nickel salts, and cobalt salts; amine salts including inorganic salts such as ammonium salts and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and Tris (hydroxymethyl)aminomethane salts; inorganic acid salts such as halide acid salts (for example hydrofluoride, hydrochloride, hydrobromide and hydriodide), nitrate, perchlorate, sulfate, and phosphate; organic acid salts including lower alkanesulfonates such as methanesulfonates, trifluoromethanesulfonates and ethanesulfonates, arylsulfonates such as benzenesulfonates and p-toluenesulfonates, acetates, malates, fumarates, succinates, citrates, tartrates, oxalates, and maleates; and amino acid salts such as glycine salts, lysine salts, arginine salts, ornithine salts, glutamates, and aspartates.

The term "pharmacologically acceptable salt thereof", as used herein, refers to salts of oligonucleotide containing at least one of nucleoside structures represented by the Formula (I) of the present invention, which are physiologically and pharmaceutically acceptable salts of the oligonucleotide of the present invention, that is, retaining a desired biological activity of the oligonucleotide and not providing an undesired toxic effect. Examples of these salts include metal salts including alkaline metal salts such as sodium salts, potassium salts, and lithium salts, alkaline earth metal salts such as calcium salts and magnesium salts, aluminum salts, iron salts, zinc salts, cuprous salts, nickel salts, and cobalt salts; amine salts including inorganic salts such as ammonium salts and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and Tris (hydroxymethyl)aminomethane salts; inorganic acid salts such as halide acid salts (for example hydrofluoride, hydrochloride, hydrobromide, hydriodide), nitrates, perchlorates, sulfates, and phosphates; organic acid salts including lower alkanesulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates, and maleates; and amino acid salts such as glycine salts, lysine salts, arginine salts, ornithine salts, glutamates, and aspartates.

Hereinafter, the present invention will be described in detail.

The oligonucleotide of the present invention includes oligonucleotides obtained through chemical modification of naturally occurring DNA or RNA Such modification changes the activity of the oligonucleotide. For example, an affinity for a target nucleic acid is improved, resistance against nucleolytic enzymes (nucleases) is improved, and the pharmacokinetics or tissue distribution of the oligonucleotide is changed. Improving the affinity of the oligonucleotide for a target may enable the use of shorter oligonucleotides.

The present invention encompasses an oligonucleotide and a pharmacologically acceptable salt thereof, which will be described below.

The oligonucleotide of the present invention includes at least one sugar-modified nucleoside at any position. This sugar-modified nucleoside includes a predetermined cross-link between position 2 and position 4 in the sugar ring. The sugar-modified nucleoside of the present invention will be described hereinafter.

The sugar-modified nucleoside of the present invention has a nucleoside structure represented by Formula (I) below:

[Chemical Formula 4]

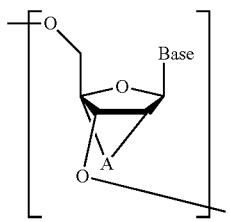
(I)

where Base represents a purin-9-yl group that may have any one or more substituents selected from group α, or a 2-oxo-1,2-dihydropyrimidin-1-yl group that may have any one or more substituents selected from group α, the group α consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms, and A is a divalent group represented by:

[Chemical Formula 5]

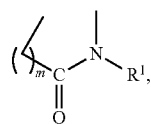
(a-1)

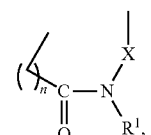
(a-2)

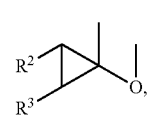
(b-1)

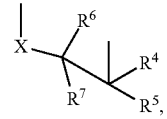
(c-1)

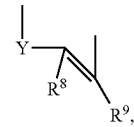
(c-2)

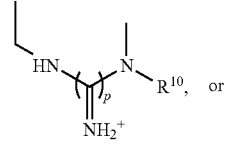
(d-1)

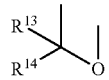
(e-1)

where $R^1$ represents a hydrogen atom, a $C_1$ to $C_7$ alkyl group that may be branched or form a ring, a $C_2$ to $C_7$ alkenyl group that may be branched or form a ring, a $C_3$ to $C_{12}$ aryl group that may have any one or more substituents selected from group α and that may contain a hetero atom, an aralkyl group having a $C_3$ to $C_{12}$ aryl moiety that may have any one or more substituents selected from group α and that may contain a hetero atom, or a protecting group for an amino group on nucleic acid synthesis;

$R^2$ and $R^3$ are independently a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom, or $R^2$ and $R^3$ are taken together to represent —$(CH_2)_q$— (where q is an integer from 2 to 5);

$R^4$ and $R^5$ are independently a group selected from the group consisting of a hydrogen atom; a hydroxy group; a $C_1$ to $C_7$ alkyl group that may be branched or form a ring; a $C_1$ to $C_7$ alkoxy group that may be branched or form a ring; an amino group; and an amino group protected by a protecting group for nucleic acid synthesis, or $R^4$ and $R^5$ are taken together to represent =$C(R^{11})R^{12}$ (where $R^{11}$ and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group);

$R^6$ and $R^7$ are independently a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^8$ represents a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^9$ is a hydrogen atom, a hydroxy group, $C_1$ to $C_7$ alkyl group that may be branched or form a ring, a $C_1$ to $C_7$ alkoxy group that may be branched or form a ring, an amino group, or an amino group protected by a protecting group for nucleic acid synthesis;

$R^{10}$ is a hydrogen atom or a guanidino group;

$R^{13}$ and $R^{14}$ are independently a group selected from the group consisting of a hydrogen atom; a hydroxy group; $C_1$ to $C_7$ alkyl group that may be branched or form a ring; a $C_1$ to $C_7$ alkoxy group that may be branched or form a ring; an amino group; and an amino group protected by a protecting group for nucleic acid synthesis;

m is an integer from 0 to 2;

n is an integer from 0 to 1;

p is 1 when $R^{10}$ is a hydrogen atom or p is 0 when $R^{10}$ is a guanidino group;

X is an oxygen atom, a sulfur atom, or an amino group; and

Y is an oxygen atom or a sulfur atom.

In an embodiment, the nucleoside structure represented by Formula (I) is a structure represented by:

[Chemical Formula 6]

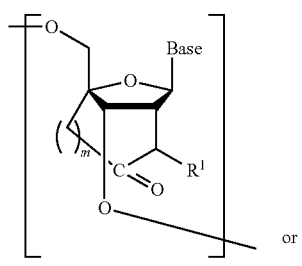

(I')

or

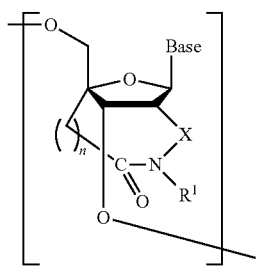

(I")

In the Formulae (I') and (I"), Base, $R^1$, X, m and n are as defined above.

In the Formulae (I') and (I"), $R^1$ represents a hydrogen atom, a $C_1$ to $C_7$ alkyl group that may be branched or form a ring, a $C_2$ to $C_7$ alkenyl group that may be branched or form a ring, a $C_3$ to $C_{12}$ aryl group that may have any one or more substituents selected from group α and that may contain a hetero atom, an aralkyl group having a $C_3$ to $C_{12}$ aryl moiety that may have any one or more substituents selected from group α and that may contain a hetero atom. More preferably, $R^1$ is a hydrogen atom, a methyl group, an ethyl group, an n-propyl group, an isopropyl group, a phenyl group, or a benzyl group. Even more preferably, $R^1$ is a hydrogen atom or a methyl group.

In the Formula (I'), m is an integer from 0 to 2; and in the Formula (I"), n is an integer from 0 to 1. Namely, the ring containing position 2', position 3', position 4' and bridged portion are 5 to 7 membered-ring.

In the Formula (I"), X is an oxygen atom, a sulfur atom, an amino group or a methylene group. Preferably, X is an oxygen atom or an amino atom. When X is an amino atom or a methylene group, it may be substituted with a lower alkyl group.

In an embodiment, the nucleoside structure represented by Formula (I) above is the structure represented by Formula (I') above where m is 0, and $R^1$ is a hydrogen atom, a methyl group, an ethyl group, an n-propyl group, an isopropyl group, a phenyl group, or a benzyl group. Such a nucleoside structure is also referred to as "amide bridged nucleic acid", "amide BNA (Bridged Nucleic Acid)", or "AmNA".

In the compounds represented by Formulae (I') and (I"), an amide bond is formed between the amino group at position 2' and a carbonyl group extending from position 4' in a sugar moiety. An amide bond, which has little structural fluctuation and excellent hydrophilicity, is provided, and therefore the structure of the sugar moiety in the nucleoside is fixed by the cross-link.

Examples of the nucleoside structure represented by Formula (I) include, in addition to the Formulae (I') and (I") mentioned above, the followings:

[Chemical Formula 7]

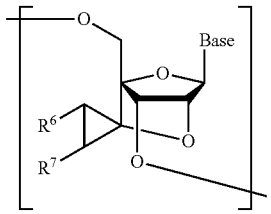

[Chemical Formula 8]

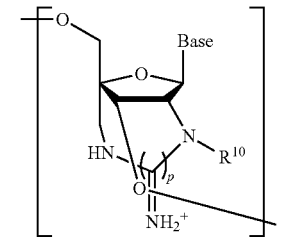

[Chemical Formula 9]

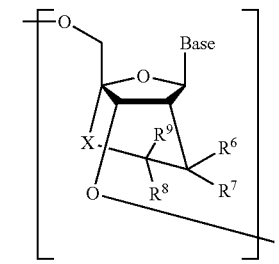

[Chemical Formula 10]

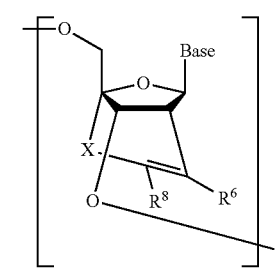

[Chemical Formula 11]

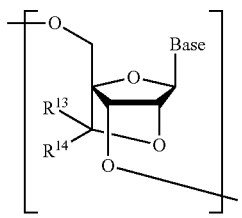

In each the Formulae mentioned above, Base, $R^6$, $R^7$, $R^8$, $R^9$, $R^{10}$, $R^{13}$ and $R^{14}$ are as defined above. Here, $R^{13}$ and $R^{14}$ are each a hydrogen atom, the nucleoside structure corresponds to a nucleoside structure referred to as 2',4'-BNA or LNA (Locked Nucleic Acid).

The "Base" mentioned above is a purine base (i.e., purine-9-yl group) or a pyrimidine base (i.e., 2-oxo-1,2-dihydropyrimidine-1-yl group). These bases may have any one or more substituents selected from group α consisting of a hydroxyl group, a $C_1$ to $C_6$ linear alkyl group, a $C_1$ to $C_6$ linear alkoxy group, a mercapto group, a $C_1$ to $C_6$ linear alkylthio group, an amino group, a $C_1$ to $C_6$ linear alkylamino group, and a halogen atom.

Specific examples of the "Base" described above include an adeninyl group, a guaninyl group, a cytosinyl group, an uracilyl group, and a thyminyl group, and a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4 mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, and a 4-amino-5-methyl-2-oxo-1,2-dihydropyrimidin-1-yl group.

Among them, considering the introduction into nucleic acid drugs, "Base" is preferably one of groups represented by the following structural formulas, respectively:

[Chemical Formula 12]

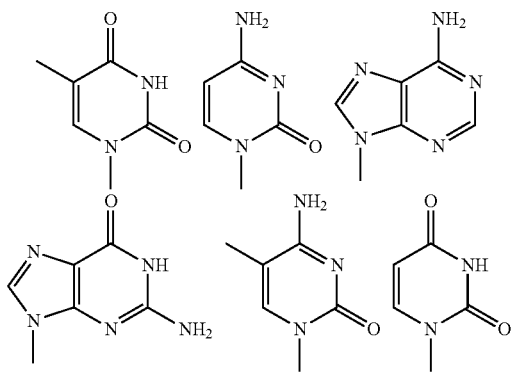

(such as a thyminyl group, a cytosinyl group, an adeninyl group, a guaninyl group, a 5-metylcytosinyl group, and an uracilyl group), and a 2-oxo-4-hydroxy-5-methyl-1,2-dihydropyrimidin-1-yl group, a 2-oxo-4-amino-1,2-dihydropyrimidin-1-yl group, a 6-aminopurin-9-yl group, a 2-amino-6-hydroxypurin-9-yl group, a 4-amino-5-methyl-2-oxo-1,2-dihydropyrimidin-1-yl group, or a 2-oxo-4-hydroxy-1,2-dihydropyrimidin-1-yl group, and more particularly a 2-oxo-4-hydroxy-5-methyl-1,2-dihydropyrimidin-1-yl group and a thyminyl group. During the synthesis of the oligonucleotides, a hydroxyl group and an amino group are preferably protected by a protective group.

The oligonucleotide including at least one sugar-modified nucleoside structure as described above can be synthesized using a sugar-modified nucleoside compound and using the methods disclosed in WO 2011/052436, JP 2014-043462A, and WO 2014/046212, for example.

An example of the sugar-modified nucleoside compound is a compound represented by Formula (II) below or a salt thereof:

[Chemical Formula 13]

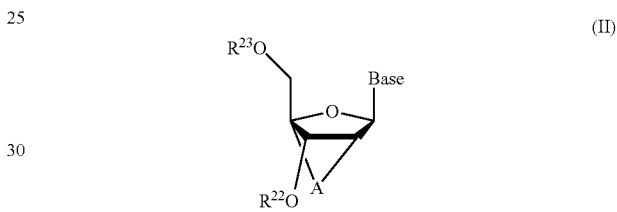

(II)

where Base represents a purin-9-yl group that may have any one or more substituents selected from group α, or a 2-oxo-1,2-dihydropyrimidin-1-yl group that may have any one or more substituents selected from group α, the group α consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms, and A is a divalent group represented by:

[Chemical Formula 14]

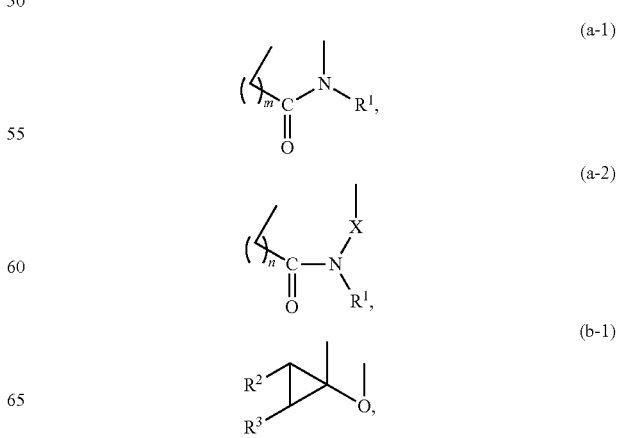

-continued

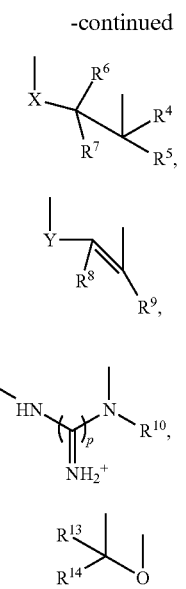

where R¹ represents a hydrogen atom, a $C_1$ to $C_7$ alkyl group that may be branched or form a ring, a $C_2$ to $C_7$ alkenyl group that may be branched or form a ring, a $C_3$ to $C_{12}$ aryl group that may have any one or more substituents selected from group α and that may contain a hetero atom, an aralkyl group having a $C_3$ to $C_{12}$ aryl moiety that may have any one or more substituents selected from group α and that may contain a hetero atom, or a protecting group for an amino group on nucleic acid synthesis;

$R^2$ and $R^3$ are independently a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom, or $R^2$ and $R^3$ are taken together to represent $-(CH_2)_q-$ (where q is an integer from 2 to 5);

$R^4$ and $R^5$ are independently a group selected from the group consisting of a hydrogen atom; a hydroxy group; a $C_1$ to $C_7$ alkyl group that may be branched or form a ring; a $C_1$ to $C_7$ alkoxy group that may be branched or form a ring; an amino group; and an amino group protected by a protecting group for nucleic acid synthesis, or $R^4$ and $R^5$ are taken together to represent $=C(R^{11})R^{12}$ (where $R^{11}$ and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group);

$R^6$ and $R^7$ are independently a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^8$ represents a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^9$ is a hydrogen atom, a hydroxy group, $C_1$ to $C_7$ alkyl group that may be branched or form a ring, a $C_1$ to $C_7$ alkoxy group that may be branched or form a ring, an amino group, or an amino group protected by a protecting group for nucleic acid synthesis;

$R^{10}$ is a hydrogen atom or a guanidino group;

$R^{13}$ and $R^{14}$ are independently a group selected from the group consisting of a hydrogen atom; a hydroxy group; $C_1$ to $C_7$ alkyl group that may be branched or form a ring; a $C_1$ to $C_7$ alkoxy group that may be branched or form a ring; an amino group; and an amino group protected by a protecting group for nucleic acid synthesis;

m is an integer from 0 to 2;

n is an integer from 0 to 1;

p is 1 when $R^{10}$ is a hydrogen atom or p is 0 when $R^{10}$ is a guanidino group;

X is an oxygen atom, a sulfur atom, or an amino group; and

Y is an oxygen atom or a sulfur atom, and $R^{22}$ and $R^{23}$ are independently a hydrogen atom, a protecting group for a hydroxyl group on nucleic acid synthesis, a $C_1$ to $C_7$ alkyl group that may be branched or form a ring, a $C_2$ to $C_7$ alkenyl group that may be branched or form a ring, a $C_3$ to $C_{12}$ aryl group that may have any one or more substituents selected from group α and that may contain a hetero atom, an aralkyl group having a $C_3$ to $C_{12}$ aryl moiety that may have any one or more substituents selected from group α and that may contain a hetero atom, an acyl group that may have any one or more substituents selected from group α, a silyl group that may have any one or more substituents selected from group α, a phosphate group that may have any one or more substituents selected from group α, a phosphate group protected by a protective group for nucleic acid synthesis, $-P(R^{24})R^{25}$ (where $R^{24}$ and $R^{25}$ each independently represent a hydroxyl group, a hydroxyl group protected by a protective group for nucleic acid synthesis, a mercapto group, a mercapto group protected by a protective group for nucleic acid synthesis, an amino group, a $C_1$ to $C_5$ alkoxy group, a $C_1$ to $C_5$ alkylthio group, a $C_1$ to $C_6$ cyanoalkoxy group, or an amino group substituted with a $C_1$ to $C_6$ alkyl group).

A sugar-modified nucleotide can be easily prepared using the sugar-modified nucleosides as described above. For example, triphosphorylation can be easily performed in accordance with the method described in M. Kuwahara et at, Nucleic Acids Res., 2008, vol. 36, No. 13, pp. 4257-65.

The oligonucleotide of the present invention can bind to the α-synuclein gene. "Binding to the α-synuclein gene" of the oligonucleotide of the present invention as used herein encompasses direct binding of the oligonucleotide of the present invention to the α-synuclein gene, binding of the oligonucleotide of the present invention to mRNA of the α-synuclein gene, and binding of the oligonucleotide of the present invention to an mRNA precursor of the α-synuclein gene.

The term "can bind to" as used herein means that a plurality of different single-stranded oligonucleotides or nucleic acids can form a nucleic acid including two or more strands due to the complementarity between the bases of the nucleic acids. Preferably, a double-stranded nucleic acid is formed. There is no particular limitation on the melting temperature ($T_m$), which is an index for the thermal stability of a bond, of the nucleic acid including two or more strands. The melting temperature ($T_m$) of a double-stranded nucleic acid can be determined as described below, for example. Equimolar amounts of an oligonucleotide and a target RNA are mixed in a buffer solution (8.1 mM $Na_2HPO_4$, 2.68 mM KCl, 1.47 mM $KH_2PO_4$, pH 7.2). The resultant mixture is heated at 95° C. for 5 minutes, and then allowed to cool slowly to room temperature for annealing to form a double-stranded nucleic acid. The temperature of the double-stranded nucleic acid is raised from 20° C. to 95° C. at a rate of 0.5° C./minute, and changes in absorbance (A) at 260 nm relative to the temperature (T) are measured. A graph of dA/dT vs T is drawn from the measurement results, and the temperature at which the value of dA/dT is the largest, that is, the temperature at which changes in A relative to T are largest, is taken as $T_m$ of the double-stranded nucleic acid. The melting temperature ($T_m$) is 40° C. or higher, for example, and preferably 50° C. or higher.

The oligonucleotide of the present invention is complementary to the α-synudein gene. However, the oligonucleotide need not be completely complementary thereto, and there may be mismatches therebetween. For example, in the oligonucleotide of the present invention and α-synudein gene, the base sequences of the regions that form a double-stranded product need not be completely complementary to each other, and there may be one or several mismatches therebetween as long as a double-stranded product can be formed and the expression inhibiting function is exhibited. The term "one or several mismatches" means one to four mismatches, preferably one to three mismatches, and more preferably one or two mismatches, which may depend on the length of the oligonucleotide. It is preferable that the oligonucleotide of the present invention is completely (100%) complementary to the base sequence of the region for forming a double-stranded product.

Examples of α-synudein (SNCA), which is a target gene of the oligonucleotide of the present invention, include human SNCA ("hSNCA") and mouse SNCA ("mSNCA"), but there is no limitation thereto.

α-Synudein ("SNCA") is a protein constituted by 140 amino acid residues, and is an amyloid protein having no specific native structure. α-Synudein is involved in the accumulation and release of synaptic vesicles. The DNA sequence (base sequence) of the human SNCA (hSNCA) coding region (GenBank accession number: NM_000345) is represented by SEQ ID No.1 in Sequence Listing, and the amino acid sequence thereof is represented by SEQ ID No.2. In the present invention, "SNCA" is not limited to these sequences, and there is no limitation on the number and positions of mutations of amino acids and DNA as long as the functions of the protein represented by SEQ ID No. 2 is maintained.

The oligonucleotide of the present invention has activity for inhibiting the expression of α-synudein gene. The SNCA expression inhibiting activity (knockdown activity) can be measured using a known method. For example, this activity can be measured using a method of transfecting an antisense oligonucleotide (ASO) into HEK293T cells (Examples 3 to 5) or a method of intraventricular administration to an α-synudein transgenic mouse (SNCA Tg mouse) (Example 6), which will be described later.

The oligonucleotide of the present invention has a length of twelve to twenty bases, for example, preferably a length of thirteen to twenty bases, more preferably a length of fourteen to twenty bases, even more preferably a length of fifteen to nineteen bases, and particularly preferably fifteen to eighteen bases. More specifically, the oligonucleotide may have a length of fifteen bases, sixteen bases, seventeen bases, or the like. When the oligonucleotide has the above-mentioned length, the oligonucleotide can more effectively bind to the target SNCA gene, or mRNA or an mRNA precursor of the target SNCA gene, and inhibit (knock down) the expression of SNCA.

In an embodiment, the oligonucleotide of the present invention can bind to a target region including a base sequence from position 99 to position 123 in SEQ ID No.1. In the human SNCA gene, the above-mentioned target region particularly relates to activity for inhibiting or knocking down the expression of the α-synudein gene.

In the present invention, the "target region" encompasses a region on the target SNCA gene (e.g., a target region including the indicated base sequence (e.g., the base sequence between position 99 and position 123 in SEQ ID No.1)) and a region on mRNA or an mRNA precursor of the SNCA gene that corresponds to the region on the gene. Moreover, the term "binding to a target region" does not necessarily refer to forming a product including two or more strands (preferably two strands) together with the entire target region, and may encompass forming a product including two or more strands (preferably two strands) together with a portion of the target region. The oligonucleotide of the present invention is complementary to at least a portion of this target region, for example, and is preferably completely complementary thereto. The "portion" as used herein is a region having a length of twelve to twenty bases in the target region. Preferably, a "partial" region can be selected as a target region so that the 3' end of the target region corresponds to position 118, position 121, or position 123 in SEQ ID No.1. "Being complementary to at least a portion of a target region" encompasses being complementary to bases of at least a portion of a target region (e.g., a region including the base sequence from position 99 to position 123 in SEQ ID No.1) on the SNCA gene and being complementary to bases of a region on mRNA or an mRNA precursor that corresponds to the at least a portion of the target region.

A preferable example of the base sequence of the oligonucleotide of the present invention is a base sequence including a portion of the base sequence of SEQ ID No.3 (an antisense oligonucleotide for a region on mRNA that corresponds to the target region including the base sequence between position 99 and position 123 in SEQ ID No.1). The sequence of the antisense oligonucleotide can be designed by arranging, in the direction from 3' toward 5' (3'→5'), bases that are complementary to the bases of the target region shown in SEQ ID No.1, the number of the bases being the number of bases (corresponding to the base length of the oligonucleotide) included in the antisense oligonucleotide. When the base sequence of the antisense oligonucleotide is shown extending in the direction from 5' toward 3' (5'→3'), the antisense oligonucleotide may be inversely complementary to the base sequence of the target region shown in SEQ ID No.1. The oligonucleotide of the present invention may be obtained through deletion, substitution, addition, or insertion of one or several bases in these sequences as long as the oligonucleotide has the SNCA expression inhibiting activity. The oligonucleotide may be preferably obtained through deletion, substitution, addition, or insertion of one to three bases, more preferably one or two bases, and even more preferably one base.

A preferable example of the oligonucleotide of the present invention is an oligonucleotide whose 5' end corresponds to a first base (corresponding to position 123 in SEQ ID No.1), a third base (corresponding to position 121 in SEQ ID No.1), or a sixth base (corresponding to position 118 in SEQ ID No.1) in SEQ ID No.3. Examples thereof include oligonucleotides with at least one sugar-modified nucleoside in the sequences of SEQ ID No.4 (fifteen bases in length), No. 5 (fourteen bases in length), No. 6 (sixteen bases in length), and No. 7 (twenty bases in length) (position 121); SEQ ID No.8 (fifteen bases in length) (position 118); and SEQ ID No.9 (fifteen bases in length) (position 123) (the position numbers in parentheses indicate the positions of the 3'-terminal bases of the target regions in the base sequence of SEQ ID No.1). For example, the oligonucleotide having the sequence of SEQ ID No.4 has the third base in SEQ ID No.3 at the 5' end, and is 15 bases in length. Moreover, the oligonucleotide having the sequence of SEQ ID No.4 is an antisense oligonucleotide whose target region is 5'-GTGTTCTCTATGTAG-3' (SEQ ID No.10) from position 107 to position 121, which is a region having a length of 15 bases and the 3' end thereof is at position 121 in the base sequence of SEQ ID No.1, and the antisense oligonucleotide is complementary to the corresponding region on mRNA and can bind thereto. The oligonucleotide of the present invention may be obtained through deletion, substitution, addition, or insertion of one or several bases in these sequences as long as the oligonucleotide has the SNCA expression inhibiting activity. The oligonucleotide may be preferably obtained through deletion, substitution, addition, or insertion of one to three bases, more preferably one or two bases, and even more preferably one base.

All of the nucleotide modifications known in the art other than the above-mentioned modification to sugar can be used in the oligonucleotide of the present invention. A modification to phosphate and a modification to a nucleic acid base are known as the nucleotide modifications. Such modifications to a nucleic acid can be performed based on methods known in the art.

Examples of the modification to phosphate include a phosphodiester bond included in a natural nucleic acid, S-oligo (phosphorothioate), D-oligo (phosphodiester), M-oligo (methylphosphonate), and boranophosphate. S-oligo (phosphorothioate) includes a PS backbone in which an oxygen atom in the phosphate group moiety of the phosphodiester bond between nucleosides is substituted by a sulfur atom. This modification is introduced into an oligonucleotide in accordance with a known method. An antisense oligonucleotide including one or more of this modification in the oligonucleotide is referred to as an S-oligo type (phosphorothioate type).

Examples of the modification to a nucleic acid base include 5-methylcytosine, 5-hydroxymethylcytosine, and 5-propynylcytosine.

There is no particular limitation on the positions and number of the sugar-modified nucleosides in the oligonucleotide of the present invention, and the oligonucleotide can be designed as appropriate depending on the purpose. Two or more sugar-modified nucleosides may be the same or different.

It is preferable that the oligonucleotide of the present invention is a gapmer. The "gapmer" means an oligonucleotide including a "gap", which is a central region, and two wings, which are regions located on both sides of the gap, namely a "5' wing" located on the 5' side and a "3' wing" located on the 3' side.

The gap region of the gapmer of the present invention may have a length of six to ten bases, preferably a length of seven to ten bases, more preferably a length of eight to ten bases, even more preferably a length of eight or nine bases, and particularly preferably a length of nine bases. The gap is constituted by native nucleosides.

The wing regions of the gapmer of the present invention may have a length of three to five bases, preferably a length of three or four bases, and more preferably three bases. In the oligonucleotide of the present invention, the "5' wing" and/or the "3' wing" includes at least one sugar-modified nucleoside. It is preferable that the "5' wing" includes at least one sugar-modified nucleoside, preferably one to five sugar-modified nucleosides, more preferably two to four sugar-modified nucleosides, even more preferably two or three sugar-modified nucleosides, and particularly preferably three sugar-modified nucleosides. It is preferable that the "3' wing" includes at least one sugar-modified nucleoside, preferably one to five sugar-modified nucleosides, more preferably two to four sugar-modified nucleosides, even more preferably two or three sugar-modified nucleosides, and particularly preferably two sugar-modified nucleosides.

In an embodiment, the gapmer may be composed of a gap region of six to ten bases, a 5' wing of three to five bases, and a 3' wing of three to five bases, the gap region being located between the 5' wing and the 3' wing, and the 5' wing and the 3' wing each containing at least one nucleoside structure represented by Formula (I) above. In addition, the gapmer may include a modification to phosphate, a modification to a base, and the like. The types, number, and positions of modifications in one wing may be the same as or different from those in the other wing.

In a preferable embodiment, the gapmer may be composed of a gap region of eight to ten bases, a 5' wing of three bases, and a 3' wing of three bases, and the 5' wing and the 3' wing each containing at least two nucleoside structures represented by Formula (I) above.

In a more preferable embodiment, the gapmer may be composed of a gap region of nine bases, a 5' wing of three bases, and a 3' wing of three bases, the three bases of the 5' wing being the nucleosides represented by Formula (I) above, and two of the three bases of the 3' wing including the nucleoside structures represented by Formula (I) above.

Examples of such a gapmer include 3-9-2-1, 3-8-2-1, 3-10-2-1, 3-10-3, and 5-10-5. For example, "3-9-2-1" refers to a gapmer in which nine bases constituting the gap are native nucleosides (DNA), the 5' wing (three bases starting from the 5' end) is constituted by sugar-modified nucleosides, two bases on the middle side of the 3' wing (three bases starting from the 3' end) are sugar-modified nucleosides, and the last base (3'-terminal base) is a native nucleoside (DNA). It is preferable to use 3-9-2-1, but this may depend on the sequence.

Examples of the oligonucleotide of the present invention include oligonucleotides having the sequences of (position 121) SEQ ID No.11 (3-9-2-1), SEQ ID No. 12 (3-8-2-1), SEQ ID No. 13 (3-10-3, 3-10-2-1), and SEQ ID No, 14 (5-10-5); (position 118) SEQ ID No.15 (3-9-2-1); and (position 123) SEQ ID No.16 (3-9-2-1) (the position numbers in parentheses indicate the positions of the 3'-terminal base of the target regions in the base sequence of SEQ ID No.1, and the gapmer regions are also shown). The oligonucleotide of the present invention may be obtained through deletion, substitution, addition, or insertion of one or several bases in these sequences as long as the oligonucleotide has the SNCA expression inhibiting activity. The oligonucleotide may be preferably obtained through deletion, substitution, addition, or insertion of one to three bases, more preferably one or two bases, and even more preferably one base.

The oligonucleotide of the present invention can be synthesized from the above-described sugar-modified nucleosides and native nucleosides using an ordinary method. For example, the oligonucleotide of the present invention can be easily synthesized using a commercially available automated nucleic acid synthesizer (manufactured by Applied Biosystems, GeneDesign Inc., or the like, for example). Solid phase synthesis using phosphoroamidite, solid phase synthesis using hydrogen phosphonate, and the like are used as the synthesis method. For example, the methods disclosed in Tetrahedron Letters, 1981, vol. 22. pp. 1859-1862, WO 2011/052436, and the like can be used.

The present invention also encompasses an α-synudein expression inhibitor containing the oligonucleotide of the present invention. Furthermore, the present invention also encompasses a pharmaceutical composition containing the oligonucleotide of the present invention. Any administration method and formulation known in the art can be used as an administration method and formulation of the α-synudein expression inhibitor or pharmaceutical composition of the present invention.

The pharmaceutical composition of the present invention can be administered using various methods for a topical or systemic treatment, or depending on regions to be treated. Examples of the administration method include topical administration (including ocular instillation, intravaginal administration, intrarectal administration, intranasal administration, and percutaneous administration), oral administration, and parenteral administration. Examples of parenteral administration include intravenous injection, intravenous instillation, subcutaneous transfusion, intraperitoneal transfusion, intramuscular transfusion, pulmonary administration through aspiration or inhalation, intraspinal administration, and intraventricular administration.

The pharmaceutical composition of the present invention can be topically administered using formulations such as a percutaneous patch, ointment, lotion, cream, gel, drops, suppository, spray, liquid medicine, and powder medicine.

Examples of compositions for oral administration include powder medicine, granular medicine, a suspension or solution obtained through dissolution in water or a non-aqueous medium, a capsule, powdered medicine, and a tablet.

Examples of compositions for parenteral administration, intraspinal administration, or intraventricular administration include sterile aqueous solutions containing a buffer, a diluent, and other appropriate additives.

The pharmaceutical composition of the present invention can be obtained by combining an effective dose of the oligonucleotide of the present invention with various pharmaceutical additives suitable for the dosage form, such as a vehicle, a binding agent, a moistening agent, a disintegrating agent, a lubricant, and a diluent as needed. In a case of an injection, the oligonucleotide is formulated with an appropriate carrier via sterilization.

Examples of the vehicle include lactose, sucrose, glucose, starch, calcium carbonate, and crystalline cellulose. Examples of the binding agent include methyl cellulose, carboxymethyl cellulose, hydroxypropyl cellulose, gelatin, and polyvinyl pyrrolidone. Examples of the disintegrating agent include carboxymethyl cellulose, sodium carboxymethyl cellulose, starch, sodium alginate, powdered agar, and sodium lauryl sulfate. Examples of the lubricant include talc, magnesium stearate, and macrogol. Cocoa butter, macrogol, methyl cellulose or the like can be used as a base for suppository. When a liquid medicine or an emulsive or suspended injection is prepared, a commonly used solubilizing agent, a suspending agent, an emulsifier, a stabilizing agent, a preservative, an isotonic agent, or the like may be added as appropriate. In a case of oral administration, a flavoring agent, an aromatic substance, or the like may be added.

The pharmaceutical composition of the present invention can be used for treatment or prevention of diseases related to the α-synudein (SNCA) gene. For example, the pharmaceutical composition of the present invention can be used for treatment or prevention based on the SNCA expression inhibiting activity (knockdown activity). An example of a disease for which the pharmaceutical composition can be used is α-synudein excess symptom. With the pharmaceutical composition of the present invention, the SNCA expression inhibiting activity (knockdown activity) can be expected to prevent the progress of neurodegeneration and the onset of dementia (particularly DLB and the like). For example, the pharmaceutical composition of the present invention can be used for treatment or prevention of Parkinson's disease or dementia with Lewy bodies.

The present invention provides a method for inhibiting the expression of α-synudein. Furthermore, the present invention also provides a method for treating or preventing α-synudein excess symptom, and a method for treating or preventing Parkinson's disease or dementia with Lewy bodies. These methods include a step of administering the oligonucleotide of the present invention to an individual. The "individual" is preferably a mammal, more preferably a human, monkey, dog, cat, rat, or mouse, and even more preferably a human. In these methods, there is no limitation on the administration method and dosage form as long as an effective dose of the oligonucleotide of the present invention is administered. Although the effective administration dose depends on the individual to which the oligonucleotide is to be administered, the effective administration dose can be determined as desired in accordance with the sex, age, weight, symptom and the like of the individual, and the method, route, frequency and the like of the administration. Examples of the administration amount include 0.1 to 10 mg/kg. The administration methods and the like are as described above.

EXAMPLES

Hereinafter, the present invention will be described by way of examples, but the present invention is not limited thereto.

Example 1

Oligonucleotide Synthesis

Oligonucleotides related to the present invention were synthesized using the methods disclosed in Tetrahedron Letters 22, 1859-1862 (1981), WO 2011/052436, and the like.

Specifically, the synthesis of oligonucleotides containing an LNA represented by Formula (a) was entrusted to GeneDesign Inc.

[Chemical Formula 15]

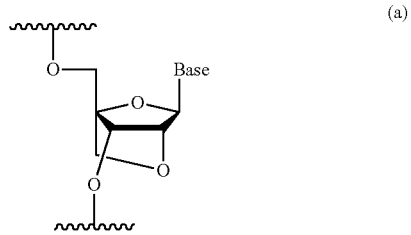

(a)

where Base is a 5-methylcytosinyl group, thyminyl group, adeninyl group, or guaninyl group.

Oligonucleotides containing an amide BNA (AmNA) represented by Formula (b) were synthesized with reference to the method disclosed in WO 2011/052436.

[Chemical Formula 16]

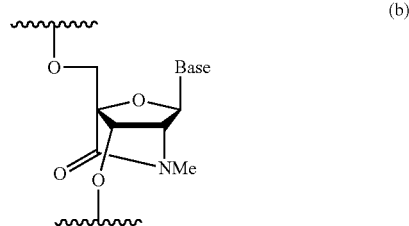

where Base is a 5-methylcytosinyl group, thyminyl group, adeninyl group, or guaninyl group, and Me is a methyl.

Oligonucleotides of 14 mer to 20 mer containing LNA represented by Formula (a) or amide BNA (AmNA) represented by Formula (b) were synthesized on 0.2 μmol scale using an automated nucleic acid synthesizer (model nS-8, manufactured by GeneDesign Inc.). The strand length was elongated in accordance with a standard phosphoroamidite protocol (solid phase support: CPG resin; DDT (3H-1,2-benzodithiole-3-one,1,1-dioxide) or the like was used for sulfurization) to obtain an oligonucleotide having a hydroxy group at the 5' end protected by DMTr (dimethoxytrityl) and at the 3' end supported on the solid phase. Next, the DMTr group was removed through acid treatment, and base treatment was performed to remove an objective product from the solid phase support. After neutralization using dilute acid, the solvent was evaporated, and then a resultant crude product was purified using gel filtration column chromatography and reversed phase HPLC. The objective product was thus obtained.

The cross-linked structure of the LNA or AmNA used in this example and the purities and structures of the obtained oligonucleotides were confirmed using HPLC and MALDI-TOF-MS (manufactured by BRUKER DALTONICS).

Example 2

Sequences of Human Antisense Oligonucleotides

Antisense oligonucleotides (AONs) were designed to target the human α-synudein (hSNCA) gene coding region (GenBank: NM_000345 (SEQ ID No.1)).

The numbers ("X" in hSNCA-X) representing the antisense oligonucleotides correspond to the base position numbers of the 3' ends of the target regions in SEQ ID No.1. For example, in the case of hSNCA-121, the 3' end of the target region is at position 121 in the base sequence of SEQ ID No.1.

The sequences of the antisense oligonucleotides were designed by determining the positions of the 3' ends of the target regions based on the base sequence of SEQ ID No.1 and arranging, in the direction from 3' toward 5' (3'→5'), bases that were complementary to the bases of the target regions by the numbers of the bases corresponding to the lengths of the antisense oligonucleotides. Therefore, when the sequences of the antisense oligonucleotides are shown extending in the direction from 5' toward 3' (5'→3'), the antisense oligonucleotides are inversely complementary to the target sequences shown by the base sequence of SEQ ID No.1. For example, in the case of the antisense oligonucleotide of hSNCA-121 having a length of 15 mer, the sequence was designed by arranging bases that were complementary to 15 bases extending toward the 5' end from position 121, namely bases from position 121 to position 107, in the base sequence of SEQ ID No.1 in the stated order. The hSNCA-121 (3-9-2-1) is an antisense oligonucleotide targeting the sequence of 5'-GTGTTCTCTATGTAG-3' (SEQ ID No.10), which is from position 107 to position 121, that is, a region of 15 bases in length with the 3' end corresponding to position 121 in the base sequence of SEQ ID No.1, and the sequence of hSNCA-121 (3-9-2-1) is 5'-CTACATAGAGAACAC-3' (SEQ ID No.11).

The gapmer configurations of the antisense oligonucleotides were designed such that sugar-modified nucleosides and native nucleosides were arranged as indicated in the descriptions of the oligonucleotides. For example, in the case of hSNCA-121 (3-9-2-1), nine bases constituting the gap region are native nucleosides (DNA), the 5' wing (three bases starting from the 5' end) is constituted by sugar-modified nucleosides, two bases on the central side of the 3' wing (three bases starting from the 3' end) are sugar-modified nucleosides, and the last base (3'-terminal base) is a native nucleoside (DNA). In the case of hSNCA-121 (5-10-5), ten bases constituting the middle region are native nucleosides (DNA), the 5' wing (five bases starting from the 5' end) is constituted by sugar-modified nucleosides, and the 3' wing (five bases starting from the 3' end) is constituted by sugar-modified nucleosides.

In addition, for comparison, oligonucleotides of Oligo ID 387985, Oligo ID 387986, and Oligo ID 388038 in Patent Document 1 were prepared. All these oligonucleotides were designed as AmNA modified 5-10-5 gapmers.

In all cases, the nucleosides were bonded by phosphorothioates (P=S) throughout the oligonucleotide.

Example 3

Primary Screening Based on Transfection of Antisense Oligonucleotide (ASO) into HEK293T Cells In this example, antisense oligonucleotides were designed as described in Example 2 and prepared as described in Example 1 such that the 3' ends of their target regions corresponded to the numbers (corresponding to the base position numbers in SEQ ID No.1) indicated on the horizontal axis in FIG. 1. The antisense oligonucleotides were prepared to contain LNAs, and have a gapmer configuration of 3-8-2-1.

Table 1 below shows the details of the prepared oligonucleotides. A, T, C, and G in the base sequences in Table 1 represent the following bases (irrespective of uppercase letters and lowercase letters; the groups represented by "Base" in Formula (a) are shown in parentheses): C, 5-methylcytosine (5-methylcytosinyl group); T, thymine (thyminyl group); A, adenine (adeninyl group); and G, guanine (guaninyl group).

TABLE 1

| No. | Name | Base Sequence* | Target region in hSNCA gene 5' end position | 3' end position | SEQ ID No. |
|---|---|---|---|---|---|
| 20 | LNA-hSNCA-20(3-8-2-1) | CCTttcatgaaTAc | 7 | 20 | 17 |
| 30 | LNA-hSNCA-30(3-8-2-1) | CTTtgaaagtcCTt | 17 | 30 | 18 |
| 40 | LNA-hSNCA-40(3-8-2-1) | CCTccttggccTTt | 27 | 40 | 19 |
| 60 | LNA-hSNCA-60(3-8-2-1) | CTCagcagcagCCa | 47 | 60 | 20 |
| 121 | LNA-hSNCA-121(3-8-2-1) | CTAcatagagaACa | 108 | 121 | 12 |
| 130 | LNA-hSNCA-130(3-8-2-1) | TTTggagcctACa | 117 | 130 | 21 |
| 140 | LNA-hSNCA-140(3-8-2-1) | CCCtccttggtTTg | 127 | 140 | 22 |
| 180 | LNA-hSNCA-180(3-8-2-1) | TTTggtcttctCAg | 167 | 180 | 23 |
| 190 | LNA-hSNCA-190(3-8-2-1) | TCActtgctctTTg | 177 | 190 | 24 |
| 200 | LNA-hSNCA-200(3-8-2-1) | CCAacatttgtCAc | 187 | 200 | 25 |
| 210 | LNA-hSNCA-210(3-8-2-1) | CACtgctcctcCAa | 197 | 210 | 26 |
| 230 | LNA-hSNCA-230(3-8-2-1) | ACTgctgtcacACc | 217 | 230 | 27 |
| 240 | LNA-hSNCA-240(3-8-2-1) | CTTctgggctaCTg | 227 | 240 | 28 |
| 250 | LNA-hSNCA-250(3-8-2-1) | CCTccactgtcTTc | 237 | 250 | 29 |
| 260 | LNA-hSNCA-260(3-8-2-1) | CTCcctgctccCTc | 247 | 260 | 30 |
| 300 | LNA-hSNCA-300(3-8-2-1) | CAActggtcctTTt | 287 | 300 | 31 |
| 310 | LNA-hSNCA-310(3-8-2-1) | CATtcttgcccAAc | 297 | 310 | 32 |
| 340 | LNA-hSNCA-340(3-8-2-1) | CCAgaattcctTCc | 327 | 340 | 33 |
| 380 | LNA-hSNCA-380(3-8-2-1) | ATTtcataagcCTc | 367 | 380 | 34 |

*5'→3' sequence, all PS backbone
Upper case letter: LNA, Lower case letter: native nucleoside On the previous day, $2.5 \times 10^5$ HEK293T cells (obtained from ATCC: ATCC CRL-1573) were seeded to 1 mL of a DMEM medium (manufactured by Thermo Fisher Scientific) supplemented with 10% FBS (containing no antibiotics) on a 12-well plate (manufactured by Thermo Fisher Scientific), including three wells and one more well for control, per oligonucleotide.

For each well, tube 1 (containing 75 µL of Opti-MEM (manufactured by Thermo Fisher Scientific) and 5 µL of Lipofectamine 2000 (manufactured by Invitrogen)) and tube 2 (containing 75 µL of Opti-MEM and 1 µL of 50 µM antisense oligonucleotide) were prepared. Tube 1 was added to tube 2, and the resultant mixture was allowed to stand at room temperature for 5 minutes and then added to the cells. The culture medium was exchanged after 4 hours, and RNA was extracted after about 24 hours.

The RNA extraction was performed using Rneasy Plus Mini Kit (manufactured by Thermo Fisher Scientific) as described below. To each well, 50 µL of buffer RLT was added and mixed. The mixture was transferred to a gDNA eliminator tube and the tube was centrifuged at 10000 rpm for 30 seconds. Next, the column in the tube was removed, 350 µL of 70% ethanol was added and mixed, and the mixture was transferred to a spin column. The spin column was centrifuged at 10000 rpm for 15 seconds, and the filtrate was discarded. Next, 700 µL of buffer RW1 was added and the spin column was centrifuged at 10000 rpm for 15 seconds. Then, 500 µL of buffer RPE was added and the spin column was centrifuged at 10000 rpm for 15 seconds. Next, 500 µL of buffer RPE was added and the spin column was centrifuged at 10000 rpm for 120 seconds. The column was placed in an Eppendorf tube, 40 µL of Rnase-free water was added thereto, and then the column was centrifuged at 10000 rpm for 60 seconds.

The reverse transcription was performed using Superscript III Kit (manufactured by Thermo Fisher Scientific) as described below. Double-distilled water (ddW) was added to 1 µg RNA to obtain a total of 8 µL of a solution, and 1 µL of Random Hexamer Primer (manufactured by Thermo Fisher Scientific) and 1 µL of 10 mM dNTP were added thereto to obtain a total of 10 µL of a solution.

When the concentration of the extracted RNA was 400 ng/µL, an aliquot of 2.5 µL of the RNA solution was taken per 1 µg of RNA, and 5.5 µL of ddW was added thereto. The resultant solution was incubated at 65° C. for 5 minutes and then allowed to stand on ice.

Master mix 1 containing 2 µL of 10× RT buffer, 4 µL of 25 mM MgCl$_2$, 2 µL of 0.1 M DTT, 1 µL RNase OUT, and 1 µL Superscript III was prepared. To each sample, 10 µL of this master mix was added, and the mixture was incubated at 25° C. for 10 minutes, at 50° C. for 50 minutes, and then at 85° C. for 5 minutes. To this mixture, 1 µL of RNase H was added, and the resultant mixture was incubated at 37° C. for 20 minutes. cDNA was thus obtained.

The quantitative PCR was performed using TaqMan (registered trademark) Gene Expression Assays (manufactured by Applied Biosystems) as described below. The obtained cDNA was 10-fold diluted with ddW (1 μL of cDNA was mixed with 9 μL of ddW). Master mix 2 was prepared by mixing Taqman Probe Mix (manufactured by Applied Biosystems), ddW, and an SNCA primer (TaqMan (registered trademark) Gene Expression Assays, ID: Hs01103383_m1) at a ratio of 10:7:1. For each cDNA 3.3 μL of diluted DNA (3.3 μL of ddW in the case of NTC) was added to 29.7 μL of master mix 2. The same procedures were performed on an 18s primer (Eukaryotic 18S rRNA Endogenous Control, manufactured by Applied Biosystems). Then, 10 μL of the mixture was dispensed into each well of a PCR plate (384 wells), and the plate was centrifuged at 2000 rpm for 5 minutes. Real-time PCR was performed using ABI PRISM 7900HT Real Time PCR Analysis System (manufactured by Applied Biosystems), and the amount of mRNA of SNCA was quantified.

Cells without transfection were used as a control.

FIG. 1 shows the results. The vertical axis in FIG. 1 indicates the amount of mRNA The amount of mRNA in the control ("Cont" in FIG. 1) was taken as 1.0, and the relative amounts of mRNA after the transfection of the antisense oligonucleotides were shown. Based on these results, antisense oligonucleotides whose target region had the 3' end corresponding to position 121 in the base sequence of SEQ ID No.1 were used in the next example.

Example 4

Secondary Screening Based on Transfection of Antisense Oligonucleotide (ASO) into HEK293T Cells Antisense oligonucleotides (ASOs) were transfected into HEK293T cells and the amounts of mRNA were measured in the same manner as in Example 3, with the exception of the following.

In this example, antisense oligonucleotides containing AmNAs and respectively having gapmer configurations of 3-10-3, 3-10-2-1, 3-9-2-1, and 5-10-5 were designed as described in Example 2 and prepared as described in Example 1 such that the 3' ends of their target regions corresponded to position 121 in the base sequence of SEQ ID No.1. For comparison, AmNA modified 5-10-5 gapmers of Oligo ID 387985, Oligo ID 387986, and Oligo ID 388038, which were mentioned in Example 2, were also used (there were mismatches between Oligo ID 388038 and four bases from position 122 to position 125 in SEQ ID No.1).

Table 2 below shows the details of the prepared oligonucleotides. A, T, C, and G in the base sequences in Table 2 represent the following bases (irrespective of uppercase letters and lowercase letters; the groups represented by "Base" in Formula (b) are shown in parentheses): C, 5-methylcytosine (5-methylcytosinyl group); T, thymine (thyminyl group); A, adenine (adeninyl group); and G, guanine (guaninyl group).

TABLE 2

| name | Base Sequence* | Target region in hSNCA gene Positions of sequence | SEQ ID No. |
|---|---|---|---|
| AmNA-hSNCA-121(3-10-3) | CTAcatagagaacAAC | positions 106 to 121 | 13 |
| AmNA-hSNCA-121(3-10-2-1) | CTAcatagagaacACc | positions 106 to 121 | 13 |
| AmNA-hSNCA-121(3-9-2-1) | CTAcatagagaaCAc | positions 107 to 121 | 11 |
| AmNA-hSNCA-121(5-10-5) | CTACatagagaacacCCTCT | positions 102 to 121 | 14 |
| 387985(5-10-5) | CCAACatttgtcactTGCTC | positions 181 to 200 | 35 |
| 387986(5-10-5) | TGTCAcacccgtcacCACTG | positions 206 to 225 | 36 |
| 388038(5-10-5) | GCCACtacatagagaACACC | positions 106 to 121 | 37 |

Figure 2:
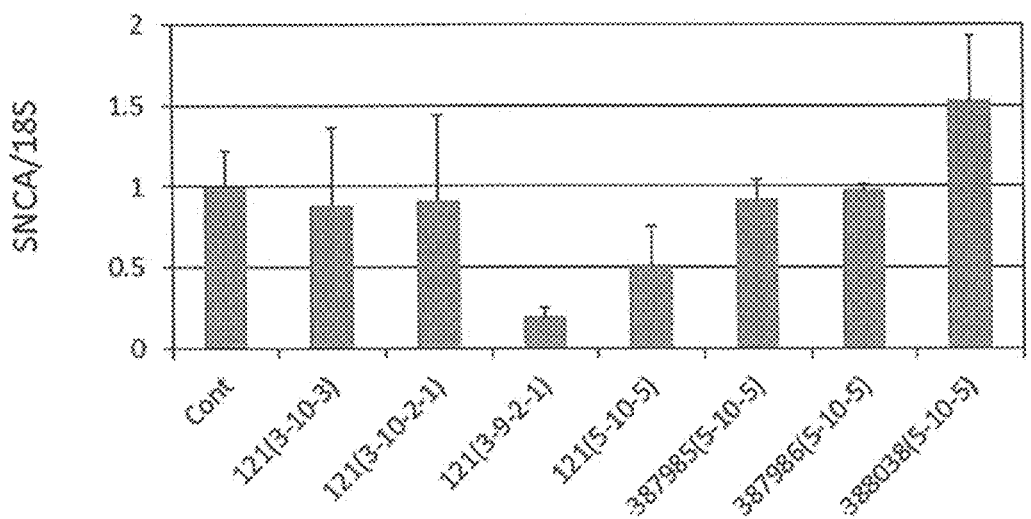
FIG. 2 is a graph showing the amounts of mRNA after the transfection of antisense oligonucleotides (ASOs) into HEK293T cells in Example 4.

*5'→3' sequence, all PS backbone
Upper case letter: AmNA, Lower case letter: native nucleoside FIG. 2 shows the results. The vertical axis in FIG. 2 indicates the amount of mRNA The amount of mRNA in the control ("Cont" in FIG. 2) was taken as 1.0, and the relative amounts of mRNA after the transfection of the antisense oligonucleotides were shown. For the antisense oligonucleotides that were tested, the 3-9-2-1 gapmer exhibited a particularly excellent α-synudein inhibiting effect. The 5-10-5 gapmer antisense oligonucleotide whose target region had the 3' end corresponding to position 121 in the base sequence of SEQ ID No.1 exhibited a better α-synudein inhibiting effect than those of the gapmers of ID387985, ID387986, and ID388038.

Example 5

Tertiary Screening Based on Transfection of Antisense Oligonucleotide (ASO) into HEK293T Cells Antisense oligonucleotides (ASOs) were transfected into HEK293T cells and the amounts of mRNA were measured in the same manner as in Example 3, with the exception of the following.

Figure 3:
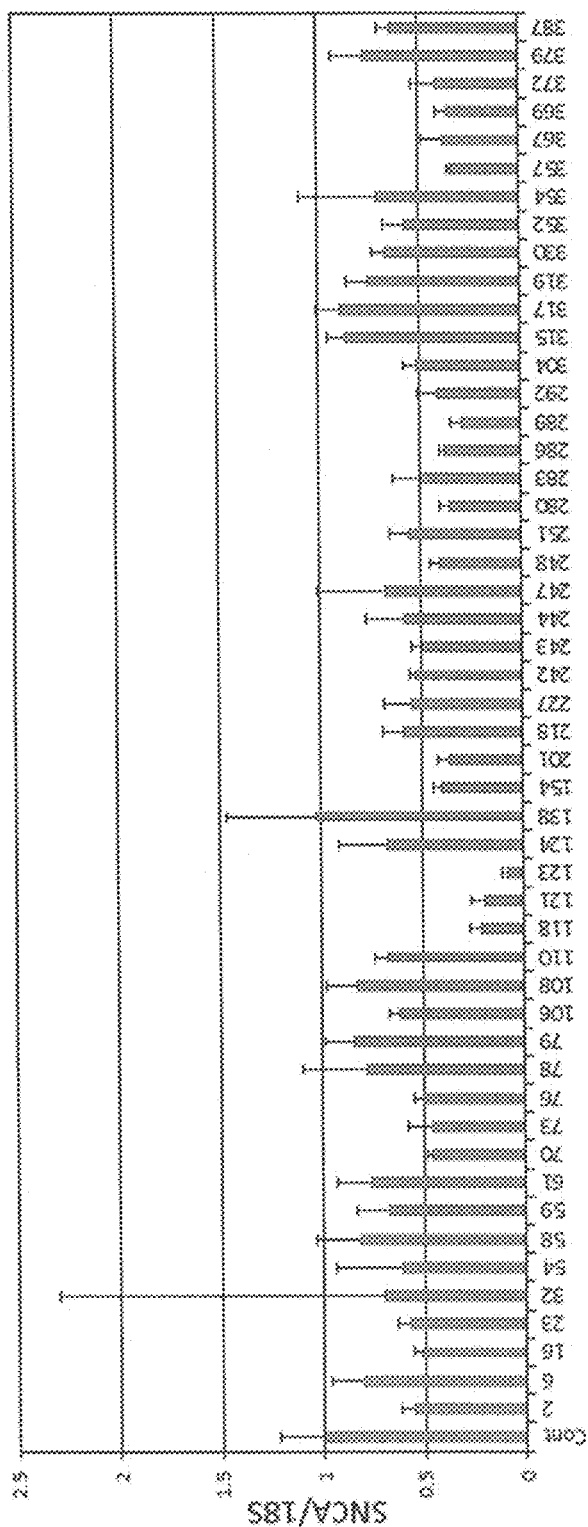
FIG. 3 is a graph showing the amounts of mRNA after the transfection of antisense oligonucleotides (ASOs) into HEK293T cells in Example 5.

In this example, antisense oligonucleotides containing AmNAs and having a gapmer configuration of 3-9-2-1 were designed as described in Example 2 and prepared as described in Example 1 such that the 3' ends of their target regions corresponded to the numbers (corresponding to the base position numbers in SEQ ID No.1) indicated on the horizontal axis in FIG. 3.

Table 3 (Tables 3-1 and 3-2) below shows the details of the prepared oligonucleotides. A, T, C, and G in the base sequences in Tables 3-1 and 3-2 are the same as those in Table 2.

TABLE 3

| No. | Name | Base Sequence* | Target region in hSNCA gene 5' end position | 3' end position | SEQ ID No. |
|---|---|---|---|---|---|
| 2 | AmNA-hSNCA-2(3-9-2-1) | ATGgctaatgaaTTc | -12 | 2 | 38 |
| 6 | AmNA-hSNCA-6(3-9-2-1) | ATCcatggctaaTGa | -8 | 6 | 39 |
| 16 | AmNA-hSNCA-16(3-9-2-1) | TCAtgaatacatCCa | 2 | 16 | 40 |
| 23 | AmNA-hSNCA-23(3-9-2-1) | AGTcctttcatgCCt | 9 | 23 | 41 |
| 32 | AmNA-hSNCA-32(3-9-2-1) | GCCtttgaaagtCCt | 18 | 32 | 42 |
| 54 | AmNA-hSNCA-54(3-9-2-1) | AGCagccacaacTCc | 40 | 54 | 43 |
| 58 | AmNA-hSNCA-58(3-9-2-1) | CAGcagcagccaCAa | 44 | 58 | 44 |
| 59 | AmNA-hSNCA-59(3-9-2-1) | TCAgcagcagccACa | 45 | 59 | 45 |
| 61 | AmNA-hSNCA-61(3-9-2-1) | TCTcagcagcagCCa | 47 | 61 | 46 |
| 70 | AmNA-hSNCA-70(3-9-2-1) | GTTtggttttctCAg | 56 | 70 | 47 |
| 73 | AmNA-hSNCA-73(3-9-2-1) | CCTgtttggttttTCt | 59 | 73 | 48 |
| 76 | AmNA-hSNCA-76(3-9-2-1) | CACcctgtttggTTt | 62 | 76 | 49 |
| 78 | AmNA-hSNCA-78(3-9-2-1) | CACaccctgtttGGt | 64 | 78 | 50 |
| 79 | AmNA-hSNCA-79(3-9-2-1) | CCAcaccctgttTGg | 65 | 79 | 51 |
| 106 | AmNA-hSNCA-106(3-9-2-1) | CCTcttttgtctTTc | 92 | 106 | 52 |
| 108 | AmNA-hSNCA-108(3-9-2-1) | ACCctcttttgtCTt | 94 | 108 | 53 |
| 110 | AmNA-hSNCA-110(3-9-2-1) | ACAccctcttttGTc | 96 | 110 | 54 |
| 118 | AmNA-hSNCA-118(3-9-2-1) | CATagagaacacCCt | 104 | 118 | 15 |
| 121 | AmNA-hSNCA-121(3-9-2-1) | CTAcatagagaaCAc | 107 | 121 | 11 |
| 123 | AmNA-hSNCA-123(3-9-2-1) | GCCtacatagagAAc | 109 | 123 | 16 |
| 124 | AmNA-hSNCA-124(3-9-2-1) | AGCctacatagaGAa | 110 | 124 | 55 |
| 138 | AmNA-hSNCA-138(3-9-2-1) | CTCcttggttttGGa | 124 | 138 | 56 |
| 154 | AmNA-hSNCA-154(3-9-2-1) | CACcatgcaccaCTc | 140 | 154 | 57 |
| 201 | AmNA-hSNCA-201(3-9-2-1) | TCCaacatttgtCAc | 187 | 201 | 58 |
| 218 | AmNA-hSNCA-218(3-9-2-1) | CCCgtcaccactGCt | 204 | 218 | 59 |
| 227 | AmNA-hSNCA-227(3-9-2-1) | GCTgtcacaccccGTc | 213 | 227 | 60 |
| 242 | AmNA-hSNCA-242(3-9-2-1) | GTCttctgggctACt | 228 | 242 | 61 |
| 243 | AmNA-hSNCA-243(3-9-2-1) | TaTcttctgggcTAc | 229 | 243 | 62 |
| 244 | AmNA-hSNCA-244(3-9-2-1) | CTGtcttctgggCTa | 230 | 244 | 63 |
| 247 | AmNA-hSNCA-247(3-9-2-1) | CCActgtattctGGg | 233 | 247 | 64 |
| 248 | AmNA-hSNCA-248(3-9-2-1) | TCCactgtcttcTGg | 234 | 248 | 65 |
| 251 | AmNA-hSNCA-251(3-9-2-1) | CCCtccactgtcTTc | 237 | 251 | 66 |
| 280 | AmNA-hSNCA-280(3-9-2-1) | AGCcagtggctgCTg | 266 | 280 | 67 |
| 283 | AmNA-hSNCA-283(3-9-2-1) | CAAagccagtggCTg | 269 | 283 | 68 |
| 286 | AmNA-hSNCA-286(3-9-2-1) | TGAcaaagccagTGg | 272 | 286 | 69 |
| 289 | AmNA-hSNCA-289(3-9-2-1) | TTTgacaaagcCAg | 275 | 289 | 70 |
| 292 | AmNA-hSNCA-292(3-9-2-1) | CCTttttgacaaAGc | 278 | 292 | 71 |
| 304 | AmNA-hSNCA-304(3-9-2-1) | TGCccaactggtCCt | 290 | 304 | 72 |

TABLE 3-continued

| No. | Name | Base Sequence* | Target region in hSNCA gene 5' end position | 3' end position | SEQ ID No. |
|---|---|---|---|---|---|
| 315 | AmNA-hSNCA-315(3-9-2-1) | TTCttcattcttGCc | 301 | 315 | 73 |
| 317 | AmNA-hSNCA-317(3-9-2-1) | CCTtcttcattcTTg | 303 | 317 | 74 |
| 319 | AmNA-hSNCA-319(3-9-2-1) | CTCcttcttcatTCt | 305 | 319 | 75 |
| 330 | AmNA-hSNCA-330(3-9-2-1) | TTCctgtggggcTCc | 316 | 330 | 76 |
| 352 | AmNA-hSNCA-352(3-9-2-1) | CAGgcatatcttCCa | 338 | 352 | 77 |
| 354 | AmNA-hSNCA-354(3-9-2-1) | CACaggcatatcTTc | 340 | 354 | 78 |
| 357 | AmNA-hSNCA-357(3-9-2-1) | ATCcacaggcatATc | 343 | 357 | 79 |
| 367 | AmNA-hSNCA-367(3-9-2-1) | CATtgtcaggatCCa | 353 | 367 | 80 |
| 369 | AmNA-hSNCA-369(3-9-2-1) | CTCattgtcaggATc | 355 | 369 | 81 |
| 372 | AmNA-hSNCA-372(3-9-2-1) | AGCctcattgtcAGg | 358 | 372 | 82 |
| 379 | AmNA-hSNCA-379(3-9-2-1) | TTTcataagcctCAt | 365 | 379 | 83 |
| 387 | AmNA-hSNCA-387(3-9-2-1) | AGAaggcatttcATa | 373 | 387 | 84 |

*5'→3' sequence, all PS backbone
Upper case letter: AmNA, Lower case letter: native nucleoside FIG. 3 shows the results. The vertical axis in FIG. 3 indicates the amount of mRNA The amount of mRNA in the control ("Cont" in FIG. 3) was taken as 1.0, and the relative amounts of mRNA after the transfection of the antisense oligonucleotides were shown. For the antisense oligonucleotides that were tested, the antisense oligonucleotides whose target regions had the 3' ends corresponding to position 118, position 121, and position 123 in the base sequence of SEQ ID No.1 exhibited a particularly excellent α-synudein expression inhibiting effect.

Example 6

Intraventricular Administration to α-Synudein Transgenic Mice (SNCA Tg Mice)

Out of the oligonucleotides shown in Table 3, the antisense oligonucleotides whose target regions had the 3' ends corresponding to position 118, position 121, and position 123 in the base sequence of SEQ ID No.1 and that contained AmNAs and had a gapmer configuration of 3-9-2-1 were used.

After SNCA Tg mice (obtained from Dr. Rikinari HANAYAMA, Osaka University Immunology Frontier Research Center; Neurobiology of Aging, 2008, vol. 29, pp. 574-585) were anesthetized with triple anesthesia, a needle was inserted to a depth of 3 mm at a position of 0.2 mm dorsalward and 1 mm to the left from the bregma in each mouse. After the needle was temporarily removed and the leakage of cerebrospinal fluid was confirmed, the needle was inserted again and 10 μL of the antisense oligonucleotide (about 1.3 mM) was injected in approximately 5 minutes. The needle was allowed to stand for 2 minutes and then removed. Next, suture was performed, and recovery from anesthesia was confirmed. One week later, the mice were sacrificed, and the left and right striate bodies, substantia nigrae, and cortices were removed from the brains and quickly frozen using liquid nitrogen.

The RNA extraction was performed using ISOGEN (manufactured by Nippon Gene Co., Ltd.) as described below. The brain tissues were mashed in liquid nitrogen, dissolved in 950 μL ISOGEN, and pipetted several times using a 21 G needle. Then, 200 μL of chloroform was added, and the resultant mixture was vortexed and centrifuged at 12000 g at 4° C. for 15 minutes. The supernatant (water layer) was transferred into 500 μL of isopropanol, and 3 μL of ethacinmate (manufactured by Nippon Gene Co., Ltd.) and 10 μL of sodium acetate were added thereto. The resultant mixture was centrifuged at 12000 g at 4° C. for 10 minutes. The supernatant was discarded, and the precipitation was washed with 500 μL of 75% ethanol and centrifuged at 7500 g at 4° C. for 5 minutes. The supernatant was discarded, and the precipitation was dissolved in 30 μL of ddW. Reverse transcription and quantitative PCR were performed in the same manner as in Example 3.

Figure 4:
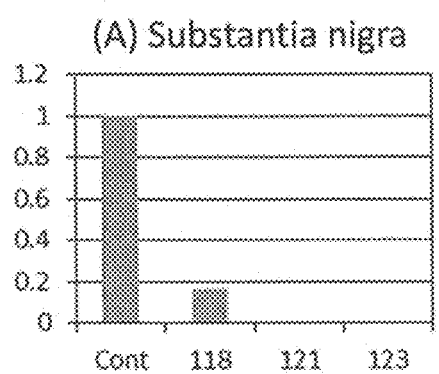
FIG. 4 shows graphs illustrating the amounts of mRNA in the substantia nigrae (a) and the striate bodies (b) after the administration of antisense oligonucleotides (ASOs) to SNCA Tg mice in Example 6.
Figure 4:
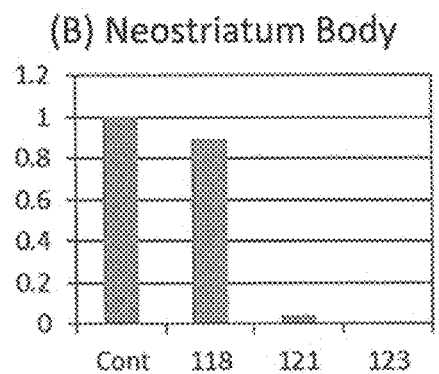

FIG. 4 shows the results. FIG. 4 shows the amounts of mRNA in the substantia nigra (a) and the striate body (b) after the administration of the antisense oligonucleotides to SNCA Tg mice. The vertical axes in FIGS. 4(a) and 4(b) indicate the amounts of mRNA. A case where the antisense oligonucleotides were not administered was taken as a control. The amount of mRNA in the control ("Cont" in FIG. 4) was taken as 1.0, and the relative amounts of mRNA after the administration of the antisense oligonucleotides were shown.

It was observed for all the antisense oligonucleotides which were administered that the amounts of mRNA in the substantia nigra and striate body were decreased compared with the control. When the intraventricular administration was performed with consideration given to the clinical application in this example, the amounts of mRNA were decreased in the striate body. Therefore, the AmNA modified oligonucleotides have excellent tissue migration properties. It is thus also expected that the AmNA modified oligonucleotides are applied via intraspinal administration for the delivery into the brain.

INDUSTRIAL APPLICABILITY

According to the present invention, oligonucleotides that are useful for inhibiting the expression of α-synudein are provided. It is expected that the oligonucleotides of the present invention will be used as nucleic acid medicines that are useful for treatment or prevention of α-synudein excess symptom, and treatment or prevention of Parkinson's disease, dementia with Lewy bodies, and the like, for example.

The invention claimed is:

1. An oligonucleotide or a pharmacologically acceptable salt thereof containing at least one nucleoside structure represented by Formula (I):

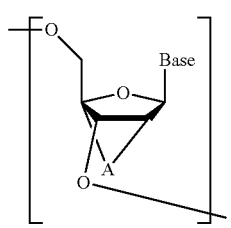

where Base represents a purin-9-yl group that may have any one or more substituents selected from group α, or a 2-oxo-1,2-dihydropyrimidin-1-yl group that may have any one or more substituents selected from group α, the group α consisting of a hydroxy group, a hydroxy group protected by a protecting group for nucleic acid synthesis, a $C_1$ to $C_6$ linear alkyl group, a $C_1$ to $C_6$ linear alkoxy group, a mercapto group, a mercapto group protected by a protecting group for nucleic acid synthesis, a $C_1$ to $C_6$ linear alkylthio group, an amino group, a $C_1$ to $C_6$ linear alkylamino group, an amino group protected by a protecting group for nucleic acid synthesis, and halogen atoms, and A is a divalent group represented by:

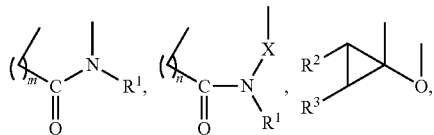

-continued

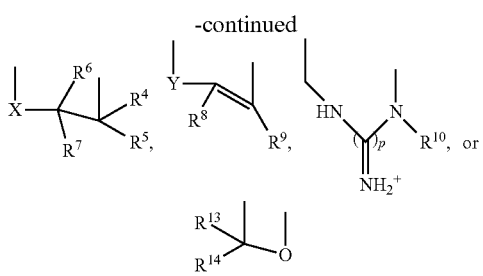

where $R^1$ represents a hydrogen atom, a $C_1$ to $C_7$ alkyl group that may be branched or form a ring, a $C_2$ to $C_7$ alkenyl group that may be branched or form a ring, a $C_3$ to $C_{12}$ aryl group that may have any one or more substituents selected from group α and that may contain a hetero atom, an aralkyl group having a $C_3$ to $C_{12}$ aryl moiety that may have any one or more substituents selected from group α and that may contain a hetero atom, or a protecting group for an amino group on nucleic acid synthesis;

$R^2$ and $R^3$ are independently a hydrogen atom; a $C_1$ to $C_7$ alkyl group that may be substituted with a $C_3$ to $C_{12}$ aryl group that may contain a hetero atom, and that may be branched or form a ring; or an aralkyl group having a $C_3$ to $C_{12}$ aryl moiety that may contain a hetero atom, or $R^2$ and $R^3$ are taken together to represent -$(CH_2)_q$-, where q is an integer from 2 to 5;

$R^4$ and $R^5$ are independently a group selected from the group consisting of a hydrogen atom; a hydroxy group; a $C_1$ to $C_7$ alkyl group that may be branched or form a ring; a $C_1$ to $C_7$ alkoxy group that may be branched or form a ring; , an amino group; and an amino group protected by a protecting group for nucleic acid synthesis, or $R^4$ and $R^5$ are taken together to represent =$C(R^{11})R^{12}$, wherein RH and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a $C_1$ to $C_6$ linear or branched alkoxy group, a $C_1$ to $C_6$ linear or branched alkylthio group, a $C_1$ to $C_6$ cyanoalkoxy group, or a $C_1$ to $C_6$ linear or branched alkylamino group;

$R^6$ and $R^7$ are independently a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^8$ represents a hydrogen atom, a $C_1$ to $C_7$ alkyl group that may be branched or form a ring, a $C_1$ to $C_7$ alkoxy group that may be branched or form a ring, or a $C_1$ to $C_6$ linear or branched alkylthio group that may be branched or form a ring;

$R^9$ is a hydrogen atom, a hydroxy group, $C_1$ to $C_7$ alkyl group that may be branched or form a ring, a $C_1$ to $C_7$ alkoxy group that may be branched or form a ring, an amino group, or an amino group protected by a protecting group for nucleic acid synthesis;

$R^{10}$ is a hydrogen atom or a guanidino group;

$R^{13}$ and $R^{14}$ are independently a group selected from the group consisting of a hydrogen atom; a hydroxy group; $C_1$ to $C_1$ alkyl group that may be branched or form a ring; a $C_1$ to $C_7$ alkoxy group that may be branched or form a ring; an amino group; and an amino group protected by a protecting group for nucleic acid synthesis;

m is an integer from 0 to 2;

n is an integer from 0 to 1;

p is 1 when $R^{10}$ is a hydrogen atom or p is 0 when $R^{10}$ is a guanidino group;

X is an oxygen atom, a sulfur atom, or an amino group; and

Y is an oxygen atom or a sulfur atom, wherein the oligonucleotide can bind to an α-synuclein gene, has activity for inhibiting expression of the α-synuclein gene, and is complementary to the α-synuclein gene, and the oligonucleotide consists of a 15-mer oligonucleotide, wherein the oligonucleotide is selected from SEQ ID Nos:11, 15, and 16.

2. The oligonucleotide or the pharmacologically acceptable salt thereof according to claim 1,
wherein the gap region has nine bases, the 5' wing and the 3' wing each has three bases, and the 5' wing and the 3' wing each contain at least two nucleoside structures represented by Formula (I).

3. The oligonucleotide or the pharmacologically acceptable salt thereof according to claim 1,
wherein the nucleoside structure represented by Formula (I) is a structure represented by:

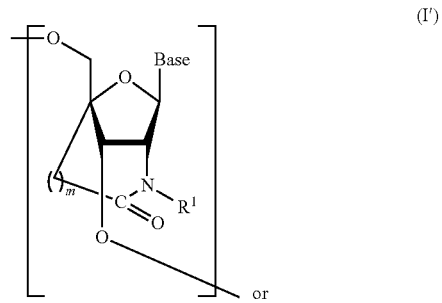

(I')

or

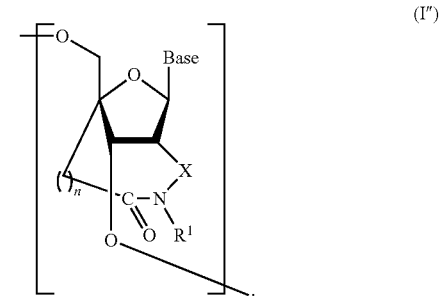

(I")

4. The oligonucleotide or the pharmacologically acceptable salt thereof according to claim 3,
wherein the nucleoside structure represented by Formula (I) is the structure represented by Formula (I') where m is 0, and $R^1$ is a hydrogen atom, a methyl group, an ethyl group, an n-propyl group, an isopropyl group, a phenyl group, or a benzyl group.

5. An α-synuclein expression inhibitor containing the oligonucleotide or the pharmacologically acceptable salt thereof according to claim 1 as an active component and a vehicle.

6. A pharmaceutical composition containing the oligonucleotide or the pharmacologically acceptable salt thereof according to any claim 1 as an active component and a vehicle.

7. The pharmaceutical composition according to claim 6, which is used for treatment of α-synuclein excess symptom.

8. The pharmaceutical composition according to claim 6, which is used for treatment of Parkinson's disease or dementia with Lewy bodies.

9. The oligonucleotide or the pharmacologically acceptable salt thereof according to claim 4, wherein $R^1$ is a methyl group.

10. An α-synuclein expression inhibitor containing the oligonucleotide or the pharmacologically acceptable salt thereof according to claim 9 as an active component and a vehicle, wherein the inhibitor is used for intraventricular administration or intraspinal administration.

11. A method for inhibiting expression of α-synuclein, the method comprising a step of administering the oligonucleotide or the pharmacologically acceptable salt thereof according to claim 1 to an individual.

12. A method for treating α-synuclein excess symptom, the method comprising a step of administering the oligonucleotide or the pharmacologically acceptable salt thereof according to claim 1 to an individual.

13. A method for treating Parkinson's disease or dementia with Lewy bodies, the method comprising a step of administering the oligonucleotide or the pharmacologically acceptable salt thereof according to claim 1 to an individual.

* * * * *

SEQUENCE LISTING

```
<160> NUMBER OF SEQ ID NOS: 84

<210> SEQ ID NO 1
<211> LENGTH: 423
<212> TYPE: DNA
<213> ORGANISM: Homo sapiens
<220> FEATURE:
<221> NAME/KEY: CDS
<222> LOCATION: (1)..(423)
<223> OTHER INFORMATION: alpha-synuclein

<400> SEQUENCE: 1 atg gat gta ttc atg aaa gga ctt tca aag gcc aag gag gga gtt gtg     48
Met Asp Val Phe Met Lys Gly Leu Ser Lys Ala Lys Glu Gly Val Val
1               5                   10                  15 gct gct gct gag aaa acc aaa cag ggt gtg gca gaa gca gca gga aag     96
Ala Ala Ala Glu Lys Thr Lys Gln Gly Val Ala Glu Ala Ala Gly Lys
                20                  25                  30 aca aaa gag ggt gtt ctc tat gta ggc tcc aaa acc aag gag gga gtg    144
Thr Lys Glu Gly Val Leu Tyr Val Gly Ser Lys Thr Lys Glu Gly Val
            35                  40                  45 gtg cat ggt gtg aca aca gtg gct gag aag acc aaa gag caa gtg aca    192
Val His Gly Val Thr Thr Val Ala Glu Lys Thr Lys Glu Gln Val Thr
        50                  55                  60 aat gtt gga gga gca gtg gtg acg ggt gtg aca gca gta gcc cag aag    240
Asn Val Gly Gly Ala Val Val Thr Gly Val Thr Ala Val Ala Gln Lys
65                  70                  75                  80 aca gtg gag gga gca ggg agc att gca gca gcc act ggc ttt gtc aaa    288
Thr Val Glu Gly Ala Gly Ser Ile Ala Ala Ala Thr Gly Phe Val Lys
                85                  90                  95 aag gac cag ttg ggc aag aat gaa gaa gga gcc cca cag gaa gga att    336
Lys Asp Gln Leu Gly Lys Asn Glu Glu Gly Ala Pro Gln Glu Gly Ile
                100                 105                 110 ctg gaa gat atg cct gtg gat cct gac aat gag gct tat gaa atg cct    384
Leu Glu Asp Met Pro Val Asp Pro Asp Asn Glu Ala Tyr Glu Met Pro
            115                 120                 125 tct gag gaa ggg tat caa gac tac gaa cct gaa gcc taa                423
Ser Glu Glu Gly Tyr Gln Asp Tyr Glu Pro Glu Ala
        130                 135                 140

<210> SEQ ID NO 2
<211> LENGTH: 140
<212> TYPE: PRT
<213> ORGANISM: Homo sapiens

<400> SEQUENCE: 2

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45
```

-continued

```
Val His Gly Val Thr Thr Val Ala Glu Lys Thr Lys Glu Gln Val Thr
     50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
        130                 135                 140
```

<210> SEQ ID NO 3
<211> LENGTH: 25
<212> TYPE: DNA
<213> ORGANISM: Artificial Sequence
<220> FEATURE:
<223> OTHER INFORMATION: alpha-synuclein antisense

<400> SEQUENCE: 3
gcctacatag agaacaccct ctttt         25

<210> SEQ ID NO 4
<211> LENGTH: 15
<212> TYPE: DNA
<213> ORGANISM: Artificial Sequence
<220> FEATURE:
<223> OTHER INFORMATION: hSNCA-121, 15 mer

<400> SEQUENCE: 4
ctacatagag aacac         15

<210> SEQ ID NO 5
<211> LENGTH: 14
<212> TYPE: DNA
<213> ORGANISM: Artificial Sequence
<220> FEATURE:
<223> OTHER INFORMATION: hSNCA-121, 14 mer

<400> SEQUENCE: 5
ctacatagag aaca         14

<210> SEQ ID NO 6
<211> LENGTH: 16
<212> TYPE: DNA
<213> ORGANISM: Artificial Sequence
<220> FEATURE:
<223> OTHER INFORMATION: hSNCA-121, 16mer

<400> SEQUENCE: 6
ctacatagag aacacc         16

<210> SEQ ID NO 7
<211> LENGTH: 20
<212> TYPE: DNA
<213> ORGANISM: Artificial Sequence
<220> FEATURE:
<223> OTHER INFORMATION: hSNCA-121, 20 mer

<400> SEQUENCE: 7
ctacatagag aaccctct         20

```
<210> SEQ ID NO 8
<211> LENGTH: 15
<212> TYPE: DNA
<213> ORGANISM: Artificial Sequence
<220> FEATURE:
<223> OTHER INFORMATION: hSNCA-118, 15 mer

<400> SEQUENCE: 8
catagagaac accct                                              15

<210> SEQ ID NO 9
<211> LENGTH: 15
<212> TYPE: DNA
<213> ORGANISM: Artificial Sequence
<220> FEATURE:
<223> OTHER INFORMATION: hSNCA-123, 15 mer

<400> SEQUENCE: 9
gcctacatag agaac                                              15

<210> SEQ ID NO 10
<211> LENGTH: 15
<212> TYPE: DNA
<213> ORGANISM: Homo sapiens

<400> SEQUENCE: 10
gtgttctcta tgtag                                              15

<210> SEQ ID NO 11
<211> LENGTH: 15
<212> TYPE: DNA
<213> ORGANISM: Artificial Sequence
<220> FEATURE:
<223> OTHER INFORMATION: hSNCA-121(3-9-2-1)

<400> SEQUENCE: 11
ctacatagag aacac                                              15

<210> SEQ ID NO 12
<211> LENGTH: 14
<212> TYPE: DNA
<213> ORGANISM: Artificial Sequence
<220> FEATURE:
<223> OTHER INFORMATION: hSNCA-121(3-8-2-1)

<400> SEQUENCE: 12
ctacatagag aaca                                               14

<210> SEQ ID NO 13
<211> LENGTH: 16
<212> TYPE: DNA
<213> ORGANISM: Artificial Sequence
<220> FEATURE:
<223> OTHER INFORMATION: hSNCA-121(3-10-3), (3-10-2-1)

<400> SEQUENCE: 13
ctacatagag aacacc                                             16

<210> SEQ ID NO 14
<211> LENGTH: 20
<212> TYPE: DNA
<213> ORGANISM: Artificial Sequence
<220> FEATURE:
<223> OTHER INFORMATION: hSNCA-121(5-10-5)

<400> SEQUENCE: 14
```
ctacatagag aacaccctct 20

<210> SEQ ID NO 15
<211> LENGTH: 15
<212> TYPE: DNA
<213> ORGANISM: Artificial Sequence
<220> FEATURE:
<223> OTHER INFORMATION: hSNCA-118(3-9-2-1)

<400> SEQUENCE: 15
catagagaac accct 15

<210> SEQ ID NO 16
<211> LENGTH: 15
<212> TYPE: DNA
<213> ORGANISM: Artificial Sequence
<220> FEATURE:
<223> OTHER INFORMATION: hSNCA-123(3-9-2-1)

<400> SEQUENCE: 16
gcctacatag agaac 15

<210> SEQ ID NO 17
<211> LENGTH: 14
<212> TYPE: DNA
<213> ORGANISM: Artificial Sequence
<220> FEATURE:
<223> OTHER INFORMATION: hSNCA-20(3-8-2-1)

<400> SEQUENCE: 17
cctttcatga atac 14

<210> SEQ ID NO 18
<211> LENGTH: 14
<212> TYPE: DNA
<213> ORGANISM: Artificial Sequence
<220> FEATURE:
<223> OTHER INFORMATION: hSNCA-30(3-8-2-1)

<400> SEQUENCE: 18
ctttgaaagt cctt 14

<210> SEQ ID NO 19
<211> LENGTH: 14
<212> TYPE: DNA
<213> ORGANISM: Artificial Sequence
<220> FEATURE:
<223> OTHER INFORMATION: hSNCA-40(3-8-2-1)

<400> SEQUENCE: 19
cctccttggc cttt 14

<210> SEQ ID NO 20
<211> LENGTH: 14
<212> TYPE: DNA
<213> ORGANISM: Artificial Sequence
<220> FEATURE:
<223> OTHER INFORMATION: hSNCA-60(3-8-2-1)

<400> SEQUENCE: 20
ctcagcagca gcca 14

<210> SEQ ID NO 21
<211> LENGTH: 14
<212> TYPE: DNA
<213> ORGANISM: Artificial Sequence
<220> FEATURE:
<223> OTHER INFORMATION: hSNCA-130(3-8-2-1)

<400> SEQUENCE: 21
ttttggagcc taca                                                14

<210> SEQ ID NO 22
<211> LENGTH: 14
<212> TYPE: DNA
<213> ORGANISM: Artificial Sequence
<220> FEATURE:
<223> OTHER INFORMATION: hSNCA-140(3-8-2-1)

<400> SEQUENCE: 22
ccctccttgg tttt                                                14

<210> SEQ ID NO 23
<211> LENGTH: 14
<212> TYPE: DNA
<213> ORGANISM: Artificial Sequence
<220> FEATURE:
<223> OTHER INFORMATION: hSNCA-180(3-8-2-1)

<400> SEQUENCE: 23
tttggtcttc tcag                                                14

<210> SEQ ID NO 24
<211> LENGTH: 14
<212> TYPE: DNA
<213> ORGANISM: Artificial Sequence
<220> FEATURE:
<223> OTHER INFORMATION: hSNCA-190(3-8-2-1)

<400> SEQUENCE: 24
tcacttgctc tttg                                                14

<210> SEQ ID NO 25
<211> LENGTH: 14
<212> TYPE: DNA
<213> ORGANISM: Artificial Sequence
<220> FEATURE:
<223> OTHER INFORMATION: hSNCA-200(3-8-2-1)

<400> SEQUENCE: 25
ccaacatttg tcac                                                14

<210> SEQ ID NO 26
<211> LENGTH: 14
<212> TYPE: DNA
<213> ORGANISM: Artificial Sequence
<220> FEATURE:
<223> OTHER INFORMATION: hSNCA-210(3-8-2-1)

<400> SEQUENCE: 26
cactgctcct ccaa                                                14

<210> SEQ ID NO 27
<211> LENGTH: 14
<212> TYPE: DNA
<213> ORGANISM: Artificial Sequence
<220> FEATURE:
<223> OTHER INFORMATION: hSNCA-230(3-8-2-1)

<400> SEQUENCE: 27
actgctgtca cacc                                                14

```
<210> SEQ ID NO 28
<211> LENGTH: 14
<212> TYPE: DNA
<213> ORGANISM: Artificial Sequence
<220> FEATURE:
<223> OTHER INFORMATION: hSNCA-240(3-8-2-1)

<400> SEQUENCE: 28
cttctgggct actg                                                      14

<210> SEQ ID NO 29
<211> LENGTH: 14
<212> TYPE: DNA
<213> ORGANISM: Artificial Sequence
<220> FEATURE:
<223> OTHER INFORMATION: hSNCA-250(3-8-2-1)

<400> SEQUENCE: 29
cctccactgt cttc                                                      14

<210> SEQ ID NO 30
<211> LENGTH: 14
<212> TYPE: DNA
<213> ORGANISM: Artificial Sequence
<220> FEATURE:
<223> OTHER INFORMATION: hSNCA-260(3-8-2-1)

<400> SEQUENCE: 30
ctccctgctc cctc                                                      14

<210> SEQ ID NO 31
<211> LENGTH: 14
<212> TYPE: DNA
<213> ORGANISM: Artificial Sequence
<220> FEATURE:
<223> OTHER INFORMATION: hSNCA-300(3-8-2-1)

<400> SEQUENCE: 31
caactggtcc tttt                                                      14

<210> SEQ ID NO 32
<211> LENGTH: 14
<212> TYPE: DNA
<213> ORGANISM: Artificial Sequence
<220> FEATURE:
<223> OTHER INFORMATION: hSNCA-310(3-8-2-1)

<400> SEQUENCE: 32
cattcttgcc caac                                                      14

<210> SEQ ID NO 33
<211> LENGTH: 14
<212> TYPE: DNA
<213> ORGANISM: Artificial Sequence
<220> FEATURE:
<223> OTHER INFORMATION: hSNCA-340(3-8-2-1)

<400> SEQUENCE: 33
ccagaattcc ttcc                                                      14

<210> SEQ ID NO 34
<211> LENGTH: 14
<212> TYPE: DNA
<213> ORGANISM: Artificial Sequence
<220> FEATURE:
<223> OTHER INFORMATION: hSNCA-380(3-8-2-1)
```

```
<400> SEQUENCE: 34
atttcataag cctc                                                    14

<210> SEQ ID NO 35
<211> LENGTH: 20
<212> TYPE: DNA
<213> ORGANISM: Artificial Sequence
<220> FEATURE:
<223> OTHER INFORMATION: 387985(5-10-5)

<400> SEQUENCE: 35
ccaacatttg tcacttgctc                                              20

<210> SEQ ID NO 36
<211> LENGTH: 20
<212> TYPE: DNA
<213> ORGANISM: Artificial Sequence
<220> FEATURE:
<223> OTHER INFORMATION: 387986(5-10-5)

<400> SEQUENCE: 36
tgtcacaccc gtcaccactg                                              20

<210> SEQ ID NO 37
<211> LENGTH: 20
<212> TYPE: DNA
<213> ORGANISM: Artificial Sequence
<220> FEATURE:
<223> OTHER INFORMATION: 388038(5-10-5)

<400> SEQUENCE: 37
gccactacat agagaacacc                                              20

<210> SEQ ID NO 38
<211> LENGTH: 15
<212> TYPE: DNA
<213> ORGANISM: Artificial Sequence
<220> FEATURE:
<223> OTHER INFORMATION: hSNCA-2(3-9-2-1)

<400> SEQUENCE: 38
atggctaatg aattc                                                   15

<210> SEQ ID NO 39
<211> LENGTH: 15
<212> TYPE: DNA
<213> ORGANISM: Artificial Sequence
<220> FEATURE:
<223> OTHER INFORMATION: hSNCA-6(3-9-2-1)

<400> SEQUENCE: 39
atccatggct aatga                                                   15

<210> SEQ ID NO 40
<211> LENGTH: 15
<212> TYPE: DNA
<213> ORGANISM: Artificial Sequence
<220> FEATURE:
<223> OTHER INFORMATION: hSNCA-16(3-9-2-1)

<400> SEQUENCE: 40
tcatgaatac atcca                                                   15

<210> SEQ ID NO 41
```

<211> LENGTH: 15
<212> TYPE: DNA
<213> ORGANISM: Artificial Sequence
<220> FEATURE:
<223> OTHER INFORMATION: hSNCA-23(3-9-2-1)

<400> SEQUENCE: 41
agtcctttca tgcct                                                          15

<210> SEQ ID NO 42
<211> LENGTH: 15
<212> TYPE: DNA
<213> ORGANISM: Artificial Sequence
<220> FEATURE:
<223> OTHER INFORMATION: hSNCA-32(3-9-2-1)

<400> SEQUENCE: 42
gcctttgaaa gtcct                                                          15

<210> SEQ ID NO 43
<211> LENGTH: 15
<212> TYPE: DNA
<213> ORGANISM: Artificial Sequence
<220> FEATURE:
<223> OTHER INFORMATION: hSNCA-54(3-9-2-1)

<400> SEQUENCE: 43
agcagccaca actcc                                                          15

<210> SEQ ID NO 44
<211> LENGTH: 15
<212> TYPE: DNA
<213> ORGANISM: Artificial Sequence
<220> FEATURE:
<223> OTHER INFORMATION: hSNCA-58(3-9-2-1)

<400> SEQUENCE: 44
cagcagcagc cacaa                                                          15

<210> SEQ ID NO 45
<211> LENGTH: 15
<212> TYPE: DNA
<213> ORGANISM: Artificial Sequence
<220> FEATURE:
<223> OTHER INFORMATION: hSNCA-59(3-9-2-1)

<400> SEQUENCE: 45
tcagcagcag ccaca                                                          15

<210> SEQ ID NO 46
<211> LENGTH: 15
<212> TYPE: DNA
<213> ORGANISM: Artificial Sequence
<220> FEATURE:
<223> OTHER INFORMATION: hSNCA-61(3-9-2-1)

<400> SEQUENCE: 46
tctcagcagc agcca                                                          15

<210> SEQ ID NO 47
<211> LENGTH: 15
<212> TYPE: DNA
<213> ORGANISM: Artificial Sequence
<220> FEATURE:
<223> OTHER INFORMATION: hSNCA-70(3-9-2-1)

<400> SEQUENCE: 47

```
gtttggtttt ctcag                                                    15

<210> SEQ ID NO 48
<211> LENGTH: 15
<212> TYPE: DNA
<213> ORGANISM: Artificial Sequence
<220> FEATURE:
<223> OTHER INFORMATION: hSNCA-73(3-9-2-1)

<400> SEQUENCE: 48
cctgtttggt tttct                                                    15

<210> SEQ ID NO 49
<211> LENGTH: 15
<212> TYPE: DNA
<213> ORGANISM: Artificial Sequence
<220> FEATURE:
<223> OTHER INFORMATION: hSNCA-76(3-9-2-1)

<400> SEQUENCE: 49
caccctgttt ggttt                                                    15

<210> SEQ ID NO 50
<211> LENGTH: 15
<212> TYPE: DNA
<213> ORGANISM: Artificial Sequence
<220> FEATURE:
<223> OTHER INFORMATION: hSNCA-78(3-9-2-1)

<400> SEQUENCE: 50
cacaccctgt ttggt                                                    15

<210> SEQ ID NO 51
<211> LENGTH: 15
<212> TYPE: DNA
<213> ORGANISM: Artificial Sequence
<220> FEATURE:
<223> OTHER INFORMATION: hSNCA-79(3-9-2-1)

<400> SEQUENCE: 51
ccacaccctg tttgg                                                    15

<210> SEQ ID NO 52
<211> LENGTH: 15
<212> TYPE: DNA
<213> ORGANISM: Artificial Sequence
<220> FEATURE:
<223> OTHER INFORMATION: hSNCA-106(3-9-2-1)

<400> SEQUENCE: 52
cctcttttgt ctttc                                                    15

<210> SEQ ID NO 53
<211> LENGTH: 15
<212> TYPE: DNA
<213> ORGANISM: Artificial Sequence
<220> FEATURE:
<223> OTHER INFORMATION: hSNCA-108(3-9-2-1)

<400> SEQUENCE: 53
accctctttt gtctt                                                    15

<210> SEQ ID NO 54
<211> LENGTH: 15
<212> TYPE: DNA
```

```
<213> ORGANISM: Artificial Sequence
<220> FEATURE:
<223> OTHER INFORMATION: hSNCA-110(3-9-2-1)

<400> SEQUENCE: 54
acaccctctt ttgtc                                                    15

<210> SEQ ID NO 55
<211> LENGTH: 15
<212> TYPE: DNA
<213> ORGANISM: Artificial Sequence
<220> FEATURE:
<223> OTHER INFORMATION: hSNCA-124(3-9-2-1)

<400> SEQUENCE: 55
agcctacata gagaa                                                    15

<210> SEQ ID NO 56
<211> LENGTH: 15
<212> TYPE: DNA
<213> ORGANISM: Artificial Sequence
<220> FEATURE:
<223> OTHER INFORMATION: hSNCA-138(3-9-2-1)

<400> SEQUENCE: 56
ctccttggtt ttgga                                                    15

<210> SEQ ID NO 57
<211> LENGTH: 15
<212> TYPE: DNA
<213> ORGANISM: Artificial Sequence
<220> FEATURE:
<223> OTHER INFORMATION: hSNCA-154(3-9-2-1)

<400> SEQUENCE: 57
caccatgcac cactc                                                    15

<210> SEQ ID NO 58
<211> LENGTH: 15
<212> TYPE: DNA
<213> ORGANISM: Artificial Sequence
<220> FEATURE:
<223> OTHER INFORMATION: hSNCA-201(3-9-2-1)

<400> SEQUENCE: 58
tccaacattt gtcac                                                    15

<210> SEQ ID NO 59
<211> LENGTH: 15
<212> TYPE: DNA
<213> ORGANISM: Artificial Sequence
<220> FEATURE:
<223> OTHER INFORMATION: hSNCA-218(3-9-2-1)

<400> SEQUENCE: 59
cccgtcacca ctgct                                                    15

<210> SEQ ID NO 60
<211> LENGTH: 15
<212> TYPE: DNA
<213> ORGANISM: Artificial Sequence
<220> FEATURE:
<223> OTHER INFORMATION: hSNCA-227(3-9-2-1)

<400> SEQUENCE: 60
gctgtcacac ccgtc                                                    15
```

<210> SEQ ID NO 61
<211> LENGTH: 15
<212> TYPE: DNA
<213> ORGANISM: Artificial Sequence
<220> FEATURE:
<223> OTHER INFORMATION: hSNCA-242(3-9-2-1)

<400> SEQUENCE: 61
gtcttctggg ctact                                                15

<210> SEQ ID NO 62
<211> LENGTH: 15
<212> TYPE: DNA
<213> ORGANISM: Artificial Sequence
<220> FEATURE:
<223> OTHER INFORMATION: hSNCA-243(3-9-2-1)

<400> SEQUENCE: 62
tgtcttctgg gctac                                                15

<210> SEQ ID NO 63
<211> LENGTH: 15
<212> TYPE: DNA
<213> ORGANISM: Artificial Sequence
<220> FEATURE:
<223> OTHER INFORMATION: hSNCA-244(3-9-2-1)

<400> SEQUENCE: 63
ctgtcttctg ggcta                                                15

<210> SEQ ID NO 64
<211> LENGTH: 15
<212> TYPE: DNA
<213> ORGANISM: Artificial Sequence
<220> FEATURE:
<223> OTHER INFORMATION: hSNCA-247(3-9-2-1)

<400> SEQUENCE: 64
ccactgtctt ctggg                                                15

<210> SEQ ID NO 65
<211> LENGTH: 15
<212> TYPE: DNA
<213> ORGANISM: Artificial Sequence
<220> FEATURE:
<223> OTHER INFORMATION: hSNCA-248(3-9-2-1)

<400> SEQUENCE: 65
tccactgtct tctgg                                                15

<210> SEQ ID NO 66
<211> LENGTH: 15
<212> TYPE: DNA
<213> ORGANISM: Artificial Sequence
<220> FEATURE:
<223> OTHER INFORMATION: hSNCA-251(3-9-2-1)

<400> SEQUENCE: 66
ccctccactg tcttc                                                15

<210> SEQ ID NO 67
<211> LENGTH: 15
<212> TYPE: DNA
<213> ORGANISM: Artificial Sequence
<220> FEATURE:

<223> OTHER INFORMATION: hSNCA-280(3-9-2-1)

<400> SEQUENCE: 67
agccagtggc tgctg                                                    15

<210> SEQ ID NO 68
<211> LENGTH: 15
<212> TYPE: DNA
<213> ORGANISM: Artificial Sequence
<220> FEATURE:
<223> OTHER INFORMATION: hSNCA-283(3-9-2-1)

<400> SEQUENCE: 68
caaagccagt ggctg                                                    15

<210> SEQ ID NO 69
<211> LENGTH: 15
<212> TYPE: DNA
<213> ORGANISM: Artificial Sequence
<220> FEATURE:
<223> OTHER INFORMATION: hSNCA-286(3-9-2-1)

<400> SEQUENCE: 69
tgacaaagcc agtgg                                                    15

<210> SEQ ID NO 70
<211> LENGTH: 15
<212> TYPE: DNA
<213> ORGANISM: Artificial Sequence
<220> FEATURE:
<223> OTHER INFORMATION: hSNCA-289(3-9-2-1)

<400> SEQUENCE: 70
ttttgacaaa gccag                                                    15

<210> SEQ ID NO 71
<211> LENGTH: 15
<212> TYPE: DNA
<213> ORGANISM: Artificial Sequence
<220> FEATURE:
<223> OTHER INFORMATION: hSNCA-292(3-9-2-1)

<400> SEQUENCE: 71
cctttttgac aaagc                                                    15

<210> SEQ ID NO 72
<211> LENGTH: 15
<212> TYPE: DNA
<213> ORGANISM: Artificial Sequence
<220> FEATURE:
<223> OTHER INFORMATION: hSNCA-304(3-9-2-1)

<400> SEQUENCE: 72
tgcccaactg gtcct                                                    15

<210> SEQ ID NO 73
<211> LENGTH: 15
<212> TYPE: DNA
<213> ORGANISM: Artificial Sequence
<220> FEATURE:
<223> OTHER INFORMATION: hSNCA-315(3-9-2-1)

<400> SEQUENCE: 73
ttcttcattc ttgcc                                                    15

-continued

```
<210> SEQ ID NO 74
<211> LENGTH: 15
<212> TYPE: DNA
<213> ORGANISM: Artificial Sequence
<220> FEATURE:
<223> OTHER INFORMATION: hSNCA-317(3-9-2-1)

<400> SEQUENCE: 74
ccttcttcat tcttg                                                    15

<210> SEQ ID NO 75
<211> LENGTH: 15
<212> TYPE: DNA
<213> ORGANISM: Artificial Sequence
<220> FEATURE:
<223> OTHER INFORMATION: hSNCA-319(3-9-2-1)

<400> SEQUENCE: 75
ctccttcttc attct                                                    15

<210> SEQ ID NO 76
<211> LENGTH: 15
<212> TYPE: DNA
<213> ORGANISM: Artificial Sequence
<220> FEATURE:
<223> OTHER INFORMATION: hSNCA-330(3-9-2-1)

<400> SEQUENCE: 76
ttcctgtggg gctcc                                                    15

<210> SEQ ID NO 77
<211> LENGTH: 15
<212> TYPE: DNA
<213> ORGANISM: Artificial Sequence
<220> FEATURE:
<223> OTHER INFORMATION: hSNCA-352(3-9-2-1)

<400> SEQUENCE: 77
caggcatatc ttcca                                                    15

<210> SEQ ID NO 78
<211> LENGTH: 15
<212> TYPE: DNA
<213> ORGANISM: Artificial Sequence
<220> FEATURE:
<223> OTHER INFORMATION: hSNCA-354(3-9-2-1)

<400> SEQUENCE: 78
cacaggcata tcttc                                                    15

<210> SEQ ID NO 79
<211> LENGTH: 15
<212> TYPE: DNA
<213> ORGANISM: Artificial Sequence
<220> FEATURE:
<223> OTHER INFORMATION: hSNCA-357(3-9-2-1)

<400> SEQUENCE: 79
atccacaggc atatc                                                    15

<210> SEQ ID NO 80
<211> LENGTH: 15
<212> TYPE: DNA
<213> ORGANISM: Artificial Sequence
<220> FEATURE:
<223> OTHER INFORMATION: hSNCA-367(3-9-2-1)
```

```
<400> SEQUENCE: 80
cattgtcagg atcca                                                    15

<210> SEQ ID NO 81
<211> LENGTH: 15
<212> TYPE: DNA
<213> ORGANISM: Artificial Sequence
<220> FEATURE:
<223> OTHER INFORMATION: hSNCA-369(3-9-2-1)

<400> SEQUENCE: 81
ctcattgtca ggatc                                                    15

<210> SEQ ID NO 82
<211> LENGTH: 15
<212> TYPE: DNA
<213> ORGANISM: Artificial Sequence
<220> FEATURE:
<223> OTHER INFORMATION: hSNCA-372(3-9-2-1)

<400> SEQUENCE: 82
agcctcattg tcagg                                                    15

<210> SEQ ID NO 83
<211> LENGTH: 15
<212> TYPE: DNA
<213> ORGANISM: Artificial Sequence
<220> FEATURE:
<223> OTHER INFORMATION: hSNCA-379(3-9-2-1)

<400> SEQUENCE: 83
tttcataagc ctcat                                                    15

<210> SEQ ID NO 84
<211> LENGTH: 15
<212> TYPE: DNA
<213> ORGANISM: Artificial Sequence
<220> FEATURE:
<223> OTHER INFORMATION: hSNCA-387(3-9-2-1)

<400> SEQUENCE: 84
agaaggcatt tcata                                                    15
```